United States Patent [19]
Neale et al.

[11] Patent Number: 5,524,133
[45] Date of Patent: Jun. 4, 1996

[54] MATERIAL IDENTIFICATION USING X-RAYS

[75] Inventors: William W. Neale, Great Wilbraham; John G. Rushbrooke, Southacre Park; Richard E. Ansorge, Cambridge, all of Great Britain

[73] Assignee: Cambridge Imaging Limited, Cambridge, Great Britain

[21] Appl. No.: 244,872

[22] PCT Filed: May 15, 1992

[86] PCT No.: PCT/GB92/00885

§ 371 Date: Jun. 13, 1994

§ 102(e) Date: Jun. 13, 1994

[87] PCT Pub. No.: WO93/14419

PCT Pub. Date: Jul. 22, 1993

[30] Foreign Application Priority Data

Jan. 15, 1992 [DE] Germany .......................... 92 00 828.3

[51] Int. Cl.⁶ .......................... G01N 23/10; G01N 23/203
[52] U.S. Cl. ............................ 378/53; 378/57; 378/70; 250/393

[58] Field of Search .................. 378/70, 71, 53, 378/83, 88, 90, 46, 51, 56, 44, 45, 46, 48, 5, 6, 7, 8, 57, 76; 250/393, 395

[56] References Cited

U.S. PATENT DOCUMENTS 4,987,584  1/1991  Doenger ............................... 378/100
5,065,418  11/1991  Bermbach et al. ..................... 378/57

Primary Examiner—Don Wong
Attorney, Agent, or Firm—Lee, Mann, Smith, McWilliams, Sweeney & Ohlson

[57] ABSTRACT

A method and apparatus for detecting the mean atomic number of a mass of material, for example freight in a vehicle comprises: subjecting the mass to X-rays and determining the mean number $N_A$ passing therethrough; subjecting the mass to higher energy X-rays and determining the new mean number $N_B$; and determining the mean atomic number of the mass from look-up tables against the computed ratio $N_A/N_B$. The mass, such as a railway wagon, may be scanned by two linear accelerators arranged perpendicular to each other, detector arrays being disposed respectively opposite the accelerators, so that a three dimensional image can be built up of the mass.

32 Claims, 11 Drawing Sheets

MATERIAL IDENTIFICATION USING X-RAYS

FIELD OF THE INVENTION

This invention concerns X-ray inspection systems and methods of X-ray inspection by which the mean atomic number of material in an object under test can be determined. The invention is of particular application in the field of baggage and container checking at ports, airports, railway marshalling yards and the like.

BACKGROUND OF THE INVENTION

It is known to use X-rays for transmission imaging in baggage scanning facilities at airports and the like.

For many reasons low energy X-rays have been employed hitherto. Not least of the reasons is the difficulty and cost of providing adequate screening for the users and the general public, which escalate as X-ray energies employed are increased. Other reasons have to do with the absorption characteristics of materials to X-rays and a greater variation is observed at low energies (for example up to 200 KeV) than is exhibited at higher energies (e.g. above 1 MeV), thereby making low energy X-ray imaging more sensitive to thickness differences.

Unfortunately low energy X-rays cannot penetrate as well as high energy X-rays and whereas the former can be used to penetrate the walls and contents of briefcases and handbags and ordinary luggage, they are of little use when containers are steel lined or made of steel as for example are shipping containers, goods waggons and the like. For such applications only high energy X-rays (in excess of 1 MeV) can be used. This has required massive concrete structures to provide the necessary shielding and because of the relatively small variation in absorption as between one material and another at such elevated energy levels, such facilities have been restricted to X-ray imaging techniques involving the production of a visual display (as on a VDU) of the interior of the object under test, which has then had to be monitored by personnel to determine if the contents are deemed to be hazardous or illegal.

Using low energy X-rays, baggage interrogation can also include determination of the mean atomic number of the materials within the container scanned. This enables a mean atomic number profile to be generated for each item. However this technique has not hitherto been possible when high energy X-rays have to be employed (to penetrate the items under inspection) since the absorption variation at these higher energies was deemed not to be sufficiently great as to admit ready discrimination between one material and another.

To this end it is an object of the present invention to provide a method and apparatus for X-ray inspection using high energy X-rays which permits discrimination on the basis of atomic number between materials exposed to the X-rays.

It is also an object of the invention to provide a method and apparatus as aforesaid by which containers such as steel shipping containers as used for road, rail and maritime freight can be X-rayed and a mean atomic number profile generated of their contents for analysis using conventional image analysis techniques, to identify the presence of particular substances or combinations of substances within the container, whereby an alarm signal can be generated if one or more criteria is satisfied, so as for example to prevent the loading or subsequent transit of a container so identified.

SUMMARY OF THE INVENTION

According to one aspect of the present invention there is provided a method of detecting the mean atomic number of a mass of material (typically within a container and therefore hidden from view) comprising the steps of:

1. subjecting the material to high energy X-rays and determining the mean number $N_A$ of X-rays transmitted through a region thereof,
2. subjecting the same region of the material to X-rays having a significantly higher energy than the first mentioned X-rays and determining the mean number $N_B$ of the higher energy X-rays transmitted therethrough,
3. computing the value of the ratio $N_A$ to $N_B$, and
4. determining from a look-up table and delivering as an output the average atomic number corresponding to the computed value of the $N_A/N_B$ ratio.

By significantly higher is meant at least twice and typically five or six times or more the energy of the first mentioned high energy X-rays. Thus if the lower high energy X-rays are of the order of 1 MeV, the higher energy X-rays will be typically of the order of 5 or 6 MeV.

In one example of the invention separate X-ray sources and X-ray detectors may be employed, spaced apart so as to reduce cross talk and interaction therebetween, and either one or both of the values of $N_A$ (obtained from the source detector combination operating at the lower energy level) and $N_B$ (obtained from the source detector combination operating at the higher energy level), is/are stored as appropriate to be available for the ratio computation step.

In another example of the invention a single broad energy band X-ray source may be employed to project a range of high energy X-rays of 1 MeV and above, towards the container. A composite detector is placed beyond the container which on bombardment by transmitted X-rays produces substantially simultaneously:

a. a first component predominently attributable to the higher energy component of the incident X-rays and b. a second component predominently attributable to the lower energy component of the incident X-rays and the energies carried by the said two components is determined; numerical values relating thereto are generated; and a ratio of one numerical value relative to the other, and, using a look-up table as aforesaid, the mean atomic number for the material through which the X-rays have passed is derived therefrom, using the value of the said ratio.

Practical composite detectors can be built using the following physical principles:

(i) The higher the X-ray energy the greater the proportion of electron-positron pair production relative to Compton scattering in the target/convertor in the detector, due to the fact that above 1 MeV the probability for the former process increases with energy while the probability of the latter decreases.

(ii) When high energy X-rays impinge on material an electromagnetic cascade is produced. The higher the energy the greater the depth at which energy may be transferred out of the electromagnetic cascade into the material.

Two methods for constructing composite detectors which use these principles are suggested.

The first enables the products of Compton scattering and pair production to be preferentially detected in separate crystals. Thus it has been noted that as the energy of X-ray photons incident on a target increases, the angular distribution of Compton scattered photons has been found to become more strongly peaked in the forward direction. Consequently photons produced by scattering due to lower energy X-rays (e.g. 1 MeV) which have passed through the container, can be detected (in preference to those produced by higher energy X-rays) by detecting photons scattered from the target at relatively large forward angles (say in the range 30° to 60°) and by disregarding forwardly projected photons (ie in the range 0° to 30°).

Likewise it has been found that when positrons produced in electron-positron pair production annihilate (a phenomenon generally associated with higher X-ray energies), photons are emitted isotropically with energy around 0.5 MeV which in the rearward direction are more numerous and have a higher energy than backwardly scattered photons produced by Compton scatter. Consequently photons attributable to higher energy X-rays transmitted through the container may be preferentially detected by detecting rearwardly propagated annihilation photons attributable to electron-positron pair production in the target, typically at an angle of 135° and greater. Thus apparatus for performing this first method comprises a target/convertor typically of tungsten and two crystals located so as to separately receive forwardly propagating photons in the range 30° to 60° off the axis and to receive rearwardly propagating photons in the range 135° to 180° off the axis.

The preferential detection may be enhanced by removing lower energy photons from the rearwardly propagating photons by filtering as by using a sheet of lead or tungsten or like material, and forcing all the rearwardly propagating photons to pass therethrough, so that only the higher energy photons reach the second detector. In this way the contribution of photons caused by Compton scattering can be substantially eliminated from the rearwardly propagating photon population.

The second method relies on the electromagnetic cascade effect produced in suitable materials when bombarded with X-rays, so that energy is transferred into the material at different depths depending on the energy of the incident X-rays.

Apparatus for performing the second method may for example comprise a sandwich of absorbers and scintillators enabling the electromagnetic cascade to be sampled at depths from the end of the sandwich on which X-rays are incident. In one embodiment the first element on which the X-ray beams impinges may comprise a relatively thin crystal, so that the energy deposited is more or less independent of X-ray energy and the spectrum of sampled X-rays is therefore strongly peaked around 1 MeV, and the thin crystal is followed by a low-z beam hardener which preferentially removes lower energy X-rays from the beam, which is then transmitted to a series of high-z converters (which favour pair production) which alternate with and are thereby sandwiched by thin crystals which sample the electrons produced by collisions upstream of the crystals. The higher the energy the further upstream will occur collisions which can be sampled, thus enhancing the probability of detection of the higher energy X-rays. Increasing the proportion of pair production increases the average energy of the secondary electrons.

Light from the crystals may be conveyed to a photoelectric device using optical fibres. Typically the outputs from all the crystals are optically coupled to give a single optical output to the photo-electric device.

Once the mean atomic number of a mass of material has been ascertained it is possible to determine from the attenuation of the X-rays at one or other energy level, the effective thickness of the material.

The invention also provides an X-ray analysis device for determining mean atomic number of a material mass as aforesaid by locating a broad band X-ray source on one side of a testing station and on the other, a detector, comprising a target having X-ray detectors positioned adjacent thereto, one of the detectors being positioned and adapted to receive X-rays scattered by the detector target in a generally rearward direction (ie in a direction back towards the source and up to 45° off the rearward axis) and the other detector being positioned and adapted to detect forwardly propagating X-rays scattered off axis typically by more than 30° and by less than 60° thereto, due to so-called Compton scatter, each of the X-ray detectors providing signals proportional to the number of X-ray photons incident thereon; means responsive to the two detector outputs forming a ratio of the number of photons detected by the two detectors and forming a numerical value thereof, a look-up table containing mean atomic numbers for given numerical ratios for different materials and means for determining from the look-up table the atomic number corresponding to the numerical ratio obtained from the outputs of the two detectors, and delivering the said atomic number (or original derived therefrom such as data giving the material name) as an output signal.

The target may be formed from tungsten and the X-ray detectors may be crystals of zinc tungstate or cadmium tungstate in which event the X-ray photons are converted by the crystals into electromagnetic radiation in the visible range and the photons of visible light can be detected and quantified using a photo-electric sensor adapted to generate from the light emitted from the crystal an electric current which can be measured to give a numerical value proportional to the X-ray photon population incident on the appropriate crystal.

Typically the source is a conventional 10 MeV electron linear accelerator with targets and beam hardeners to determine the X-ray spectrum emanating therefrom.

Although reference has been made to the source and detector as being on opposite sides of the mass under test, it is to be understood that this includes above and below as well as left and right or any other orientation.

As so far described the method and apparatus will only permit one reading to be taken for an article located between the source and the detector and is therefore limited in application to testing relatively small items or quantities of material.

In order to permit larger items to be inspected such as a freight container or railway waggon or road vehicle, the X-rays from the source are preferably collimated into a divergent but narrow beam, which since the actual source is relatively small and can be thought of as a point, can be likened to a fan extending in a generally vertical plane from the point source, and a plurality of detectors are positioned in an array in the same vertical plane on the remote side of a testing station each pointing towards the source and preferably to the point from which the fan of X-rays emanates, and each distanced therefrom by approximately the same length, the two X-ray sensitive crystals associated with each detector being separately addressable to determine the photon population seen by them, for determining the ratio as aforesaid for each detector means being provided for memorising the ratio obtained from each detector to enable a profile to be produced of all of the ratios seen by all of the detectors in the array.

Such an apparatus will allow analysis of the mean atomic number of material making up different regions of an object, and will enable for example the variation in composition as between one region and another of such an object to be determined.

If relative movement between the inspection means and the object is introduced, generally perpendicular to the plane of the X-ray beam, an object can effectively be scanned from one end to the other, and by memorising the signals obtained during the lengthwise scanning, so a two-dimensional profile can be obtained for the whole object as viewed by the detector.

If the object cannot be moved (for example is a building) the X-ray source and the array of detectors must be moved synchronously on opposite sides of the object.

If the object is mobile (as is normally the case), more preferably the source and the detector array are aligned and fixed in position and the object is moved steadily therebetween, the source and detector array being located either on opposite sides of the object, or above and below the object.

The fixing of the source and detectors has the added advantage that they can more readily be housed for the purpose of shielding which since high energy X-rays are involved is of considerable importance.

If a three-dimensional composition profile of an object is required, a second source detector combination may be located perpendicular to the first source/detector combination, so that the narrow beam of the second source propagates through the object in the same (or a parallel) plane as that occupied by the first beam but with the central axes of the two beams at right angles.

If the first source and detector array is located on opposite sides of the testing station, the second source is typically located above, and the second detector array below, the testing station, so that a composition profile of the object can be obtained for each of the inspected "slices", across its width, as well as from top to bottom thereof. With relative movement a series of "slices" is built up and a true three dimensional profile of the material making up the object can be obtained, allowing in some cases the size and even shape of components or contents of differing material composition to be determined.

Electrical signals corresponding to the two profiles, typically are stored, so that they can be employed to control a visual display to allow cross-sections of for example a rectilinear container to be displayed showing material variation therein as viewed from side to side, from top to bottom, and from end to end, of the container as desired. In addition or alternatively the signals may be combined to permit for example a series of three dimensional isometric views of the container to be displayed with the nearside end face in each container corresponding to the cross-section that would be seen if the container were to be cut in two in a vertical plane and the nearer portion of the container removed thereby leaving a cut face of the container exposed. By presenting such a series of views in sequence at the rate of for example four or five per second or even faster, so a visual three-dimensional picture of the interior of the container can be built up allowing the size and shape of objects of differing material composition therewithin to be ascertained.

By comparing the image data in each slice with the next, it is possible for a computer to determine any image content which is constant and appears in the same position in each "slice". Such items may for example comprise end to end beams, the walls of a container, and the like, and data relating thereto can either be enhanced in the final image (by displaying it in each cross-section in the same distinguishing colour, for example black) or rendered invisible, leaving for example only the internal contents of a container visible.

This principle also may be applied to the contents in that if a container is filled for example with grain but buried in the grain is a small metal box, the computer may be programmed to disregard the steel struts and plates making up the container and also disregard the substantially continuous data representing the grain but to display data arising from the intersection of X-rays with the small steel box.

The invention is thus of considerable value in ascertaining the contents of containers both from the aspect of security and of smuggling, and may permit non intrusive inspection of all goods crossing a border or passing through a port for comparison with the accompanying documentation.

Although the X-ray detectors have been described as being crystals of material which will produce light when X-rays are incident thereon, the crystals may alternatively comprise materials which will generate electrical signals direct from incident X-rays.

Where light emitting crystals are employed, light collection means is preferably provided to gather light emitted by each crystal and light guide means may be provided such as an optical glass or plastic fibre, for conveying the light to an intensified CCD camera or the like. An intensified CCD camera may be employed if the light guides from a large number of detectors in the array terminate at differently addressable points over the surface of the CCD camera in which event very low light levels and therefore X-ray emissions may be detected using the light integrating properties of such a device. In this event scanning after a suitable period of time has elapsed permits integration of photons arriving thereon all as described in UK Patent Specification No. 2204770.

In mounting a line of detectors as aforesaid in close spatial relationship, the X-rays emitted by each target can seriously affect the outputs from crystals of adjoining detectors. Whilst it is possible to design screening to overcome this, an alternative and possibly more preferable arrangement involves the positioning of the detectors in two or more (typically four or five) different arcs also centred on the same point (the X-ray source) but having successively increased radii of curvature, and locating adjoining detectors on different ones of the arcs. By selecting the radial spacing between arcs to be great enough to reduce cross talk between the closest of the targets and unrelated detectors to say 1 part in 1000 or less (which for 5 to 6 MeV X-rays is typically 100 mm), a simple and effective detector array can be constructed without expensive screening.

Variation as between one detector and another and the variation in path length and therefore signal between source and detectors (due to the positioning of detectors on different arcs) can be calibrated out by scanning a large homogeneous object of known material.

The invention also lies in a freight checking facility incorporating at least one X-ray source/detector combination as aforesaid and means for computing the ratios of detector two output signals from each detector and determining the mean atomic number of the material exposed to the X-rays which further comprises:

(a) a housing or building surrounding the X-ray source(s) and X-ray detectors for absorbing any X-rays not absorbed by the material under test or by the detectors, (b) entrance and exit doors, (c) a path leading to the entrance, extending through the housing or building and leaving through the exit which in the housing or building extends between the source(s) and the detectors, to enable freight to move into, through and out of the housing or building, (d) at least two paths beyond the exit with means for diverting freight which has been scanned onto one or the other of the two paths, the length of each of the two paths being such as to permit all of a group of linked items of freight (as for example a train made up of trucks each carrying freight) to be contained wholly thereon, (e) means by which freight from either of said two paths can be moved onto a single ongoing path beyond the section containing the at least two paths, and (f) means for preventing an item of freight (or group of linked items) from leaving the path onto which it has been conveyed if an alarm signal generated in response to the earlier scanning of the freight on that path, whereby an item of freight which has to be physically checked because of what has been seen during the scanning need not impede the ongoing progress of other items of freight (typically other trains) which do not cause alarm signals to be generated.

This arrangement is of particular importance when considering the checking of independently pulled freight trains and in which the paths are railway tracks, since for speed and safety it is important that trains which do not produce an alarm signal (which in practice will comprise the majority) can pass uninterruptedly through the checking facility and beyond.

In a typical facility a linear accelerator operating at 10 MeV together with various targets and beam hardeners is employed, a collimator serves to define a fan beam of small width of the order of a few millimeters, and a path such as a railway track, roadway or conveyor extends perpendicular to the axis of the beam at a distance of typically 10 meters from the source target. Another collimator is located on the other side of the path to eliminate scattered X-rays which are not within the width of the fan and beyond the second collimator is situated an array of converters, crystals and absorbers are arranged in a manner so as to reduce cross talk between one crystal and another to a level of approximately one part in one thousand and optical fibre means (or electrical conductor means if the crystals generate electrical signals) leading to a device by which each crystal output can be scanned in turn and a value obtained therefrom corresponding to the X-ray photon population incident on the crystal concerned.

In typical applications, such as freight containers, the container wall is several millimeters thick and is usually formed from steel and typical contents have an absorption equivalence of typically some tens of centimeters of steel. Using as an example 50 mm of steel, it can be shown that using relatively low energy X-rays of the order of 100 KeV, only 1 part in 1,000,000 of the original source X-rays will be transmitted. On the other hand if the energy is raised to 1 MeV, approximately one tenth of the X-ray energy incident on the article will be transmitted and at this level X-ray imaging becomes possible.

As mentioned it is normally desirable to gain a knowledge of the contents of a container which are hidden from view, so as to detect for explosive devices, guns, contraband, drugs etc. Examination of transmission X-ray images can give an insight into the different materials present through shape, shading and even depth information where stereoscopic or orthogonal scanning is employed. However this is usually insufficient to enable automated analysis to be performed to eliminate from detailed consideration all but a very small number of containers under examination, and an actual knowledge of the atomic number of the materials is desirable.

At low energy levels (typically of the order of 100 KeV) X-ray transmission imaging as used in baggage scanning at airports can enable discrimination between organic materials having mean atomic numbers of the order 6, 7 or 8 and metallic materials having atomic numbers typically above 12.

Material discrimination arises from the energy dependence of the transmission co-efficient being different for different materials. The transmitted X-rays are detected by pairs of crystals placed one behind the other the front crystal being sensitive to lower energy X-rays while the rear crystal is sensitive to higher energy X-rays, lower energy X-rays being filtered out using appropriate screens. Good discrimination is possible at low X-ray energies because of the strong variation with energy of the transmission co-efficient for the crystals of the X-ray detectors. The X-rays are absorbed by the photoelectric process which has a strong energy dependence. For example in caesium iodide the transmission co-efficient changes by a factor of 6 as between 50 KeV and 100 KeV.

At higher energies (as already mentioned) of the order of 1 MeV and above, all crystal materials show a relatively weak energy dependence of transmission co-efficient. For example between 1 MeV and 5 MeV the transmission co-efficient for zinc tungstate changes by a factor of only 1.7. Even with optimum crystal thickness, useful materials discrimination is hardly achievable especially when silicon photodiodes are employed to detect the scintillation light in the crystals, caused by incident X-rays.

The invention overcomes these problems by deriving the ratio of the transmissivity of a material under test to lower energy X-rays relative to that at higher energy X-rays (typically 1 Mev and 5 MeV) which ratio has been found to vary steadily and distinguishably from one material to another, so that atomic number of materials can be plotted against ratios and a look-up table created, so that having arrived at a ratio for a given material, its mean atomic number can be obtained quickly and accurately.

The invention also overcomes the problem of noise by proposing crystals which scintillate when subjected to X-rays, and conveying the scintillation light from each crystal via optical fibres to an intensified CCD camera as described in UK Patent Specification No. 2204770.

Inspection apparatus according to the invention can be programmed to generate an alarm signal in the event that certain ratio values are detected (for example corresponding to drugs, explosives and the like) or certain combinations of ratio values are detected within the same container such as for example make up the components of a timed explosive device which will generally include a battery, fuse, explosive and timing device. Other alarm conditions may be detected in the event that sudden transitions between one ratio value and another are detected when for example containers are supposed to contain substantially the same material and can be considered to be substantially homogeneous.

The invention will now be described by way of example with reference to the accompanying drawings in which.

Figure 7:
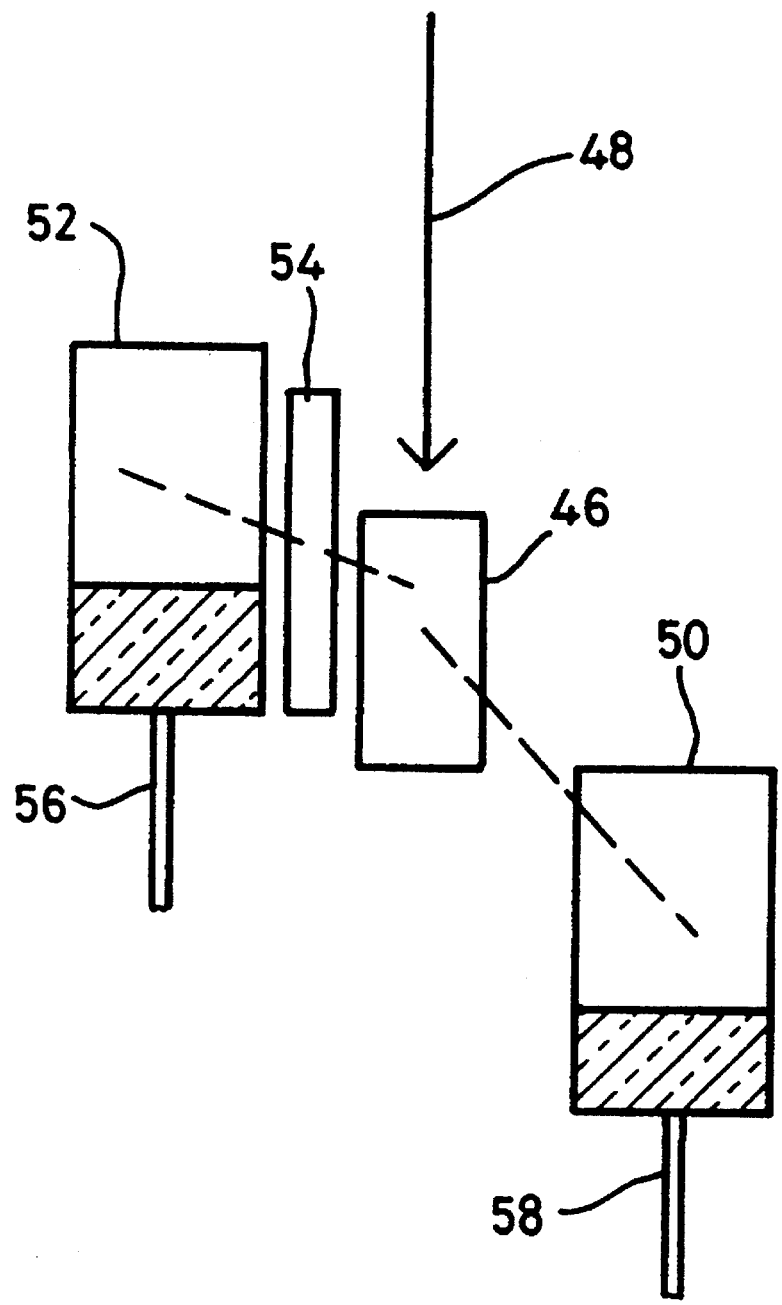
FIG. 7 is a schematic plan view of a detector element such as may be employed in the column of detectors in FIG. 6.
Figure 10A:
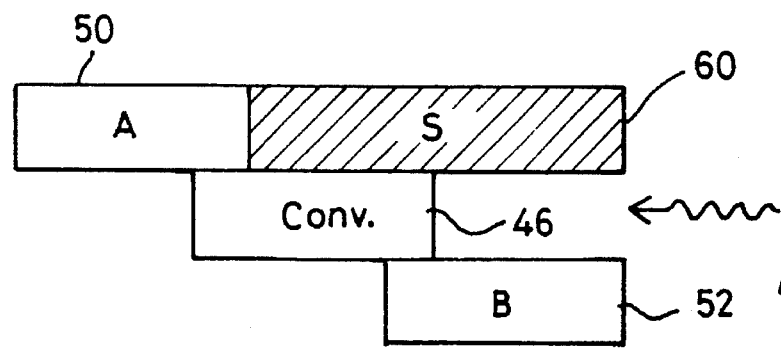
Figure 11:
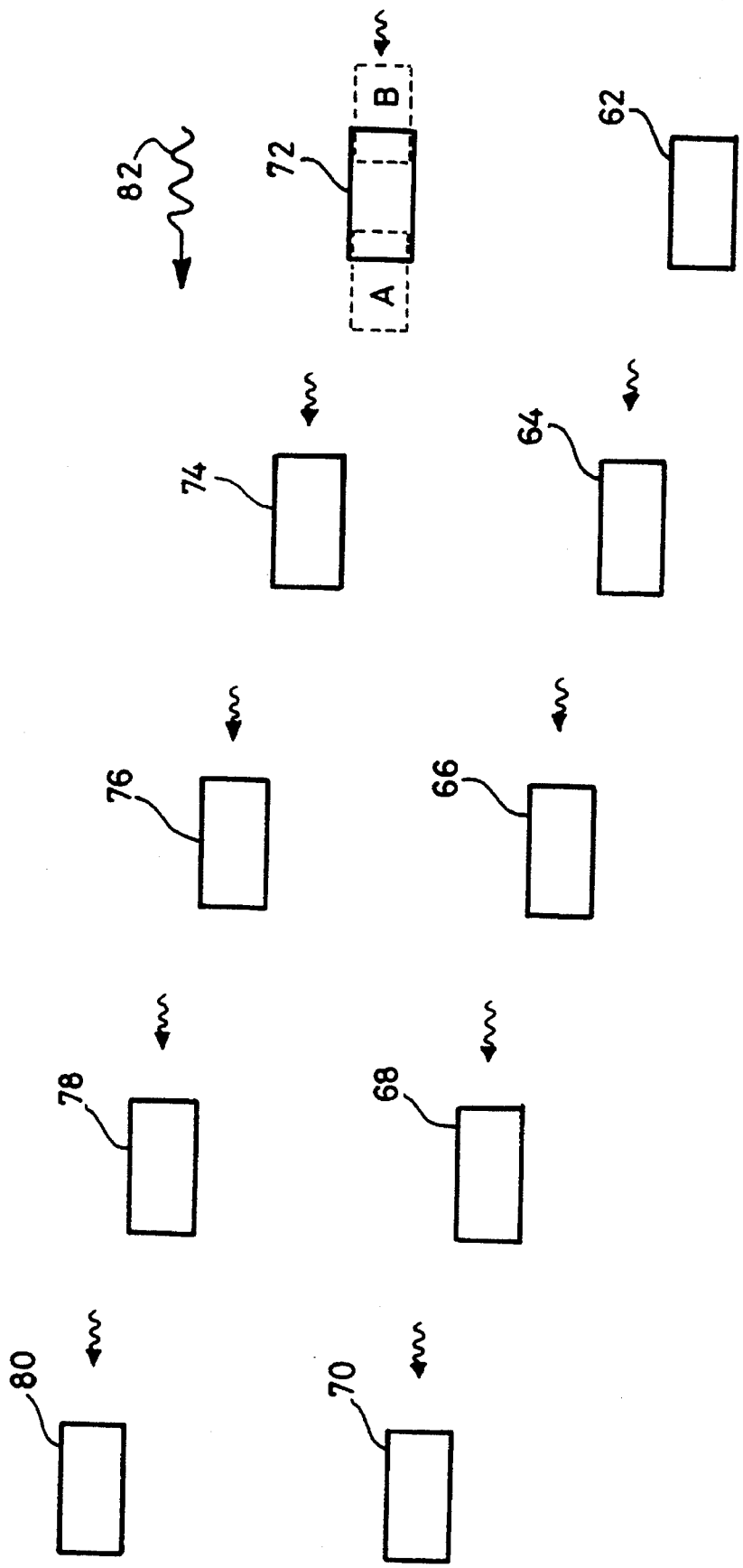
Figure 12:
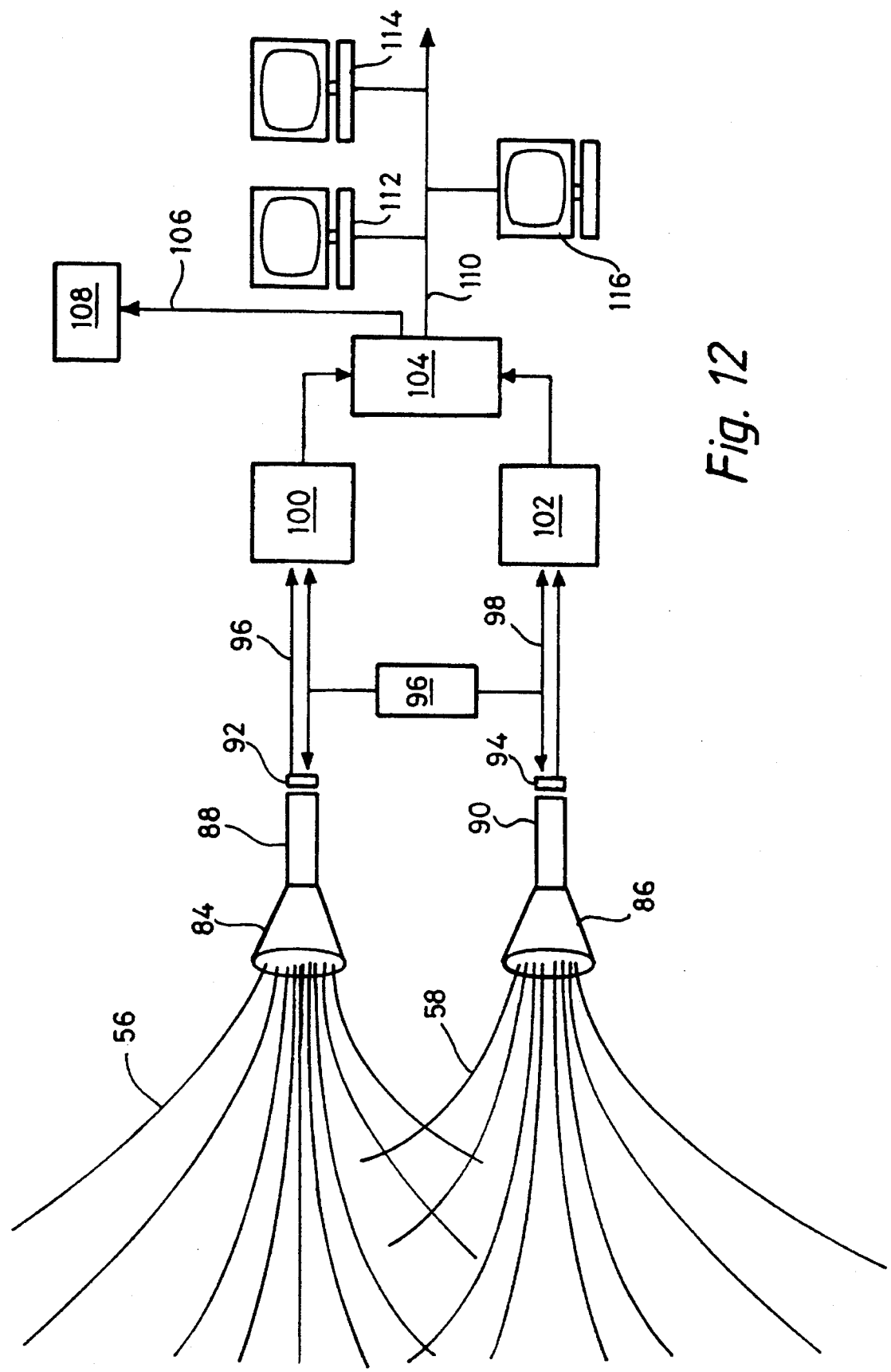
Figure 13:
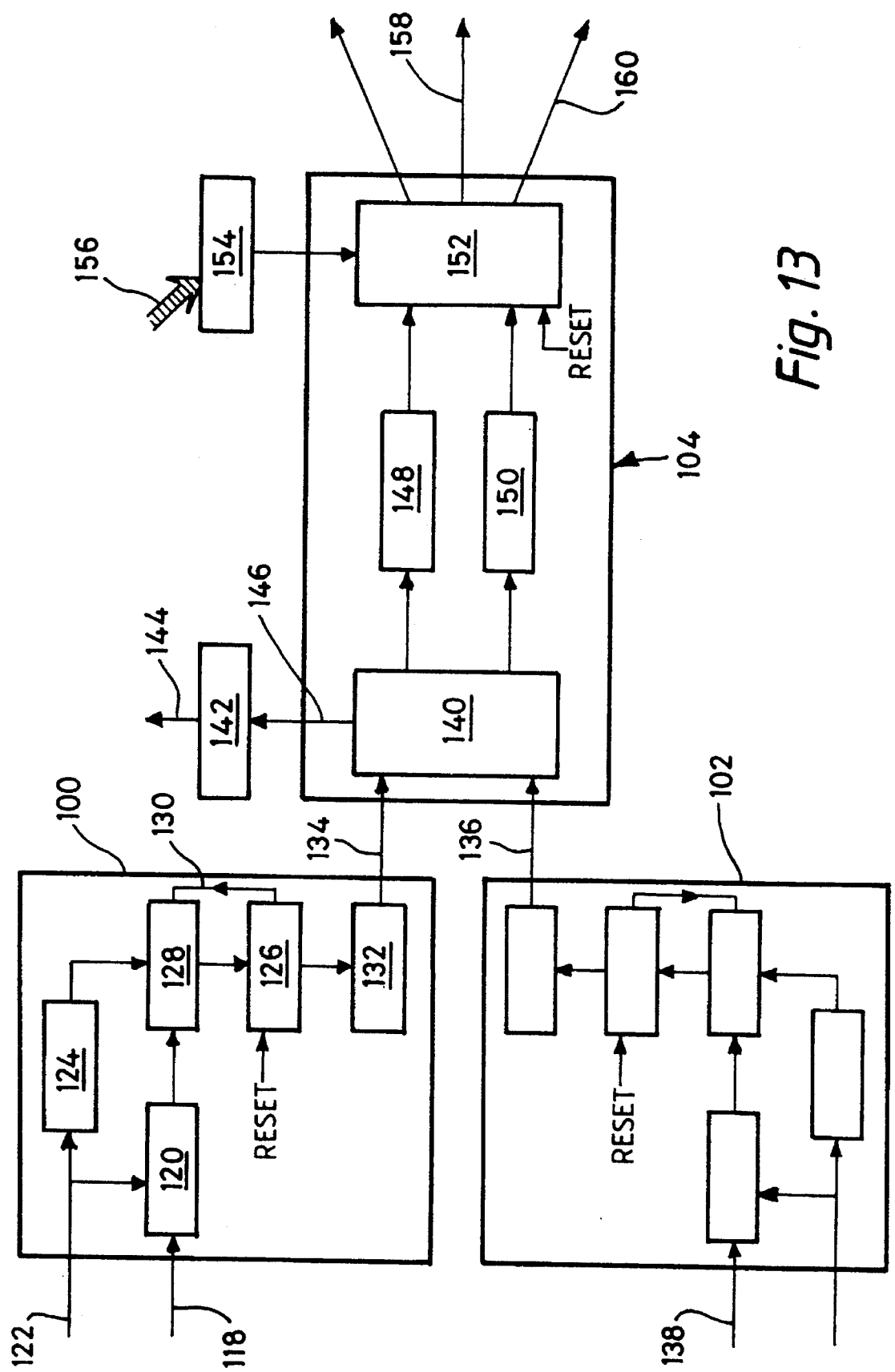
Figure 14:
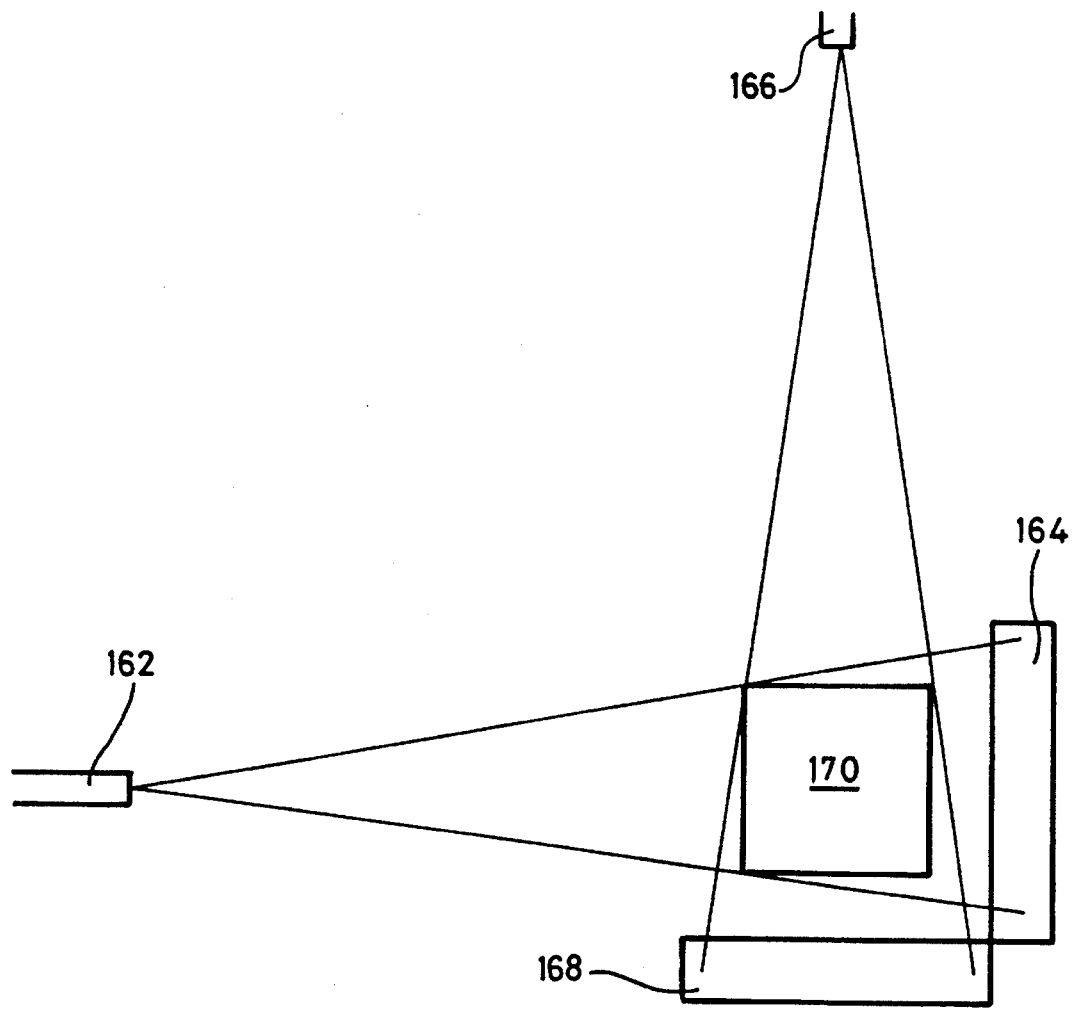
Figure 15:
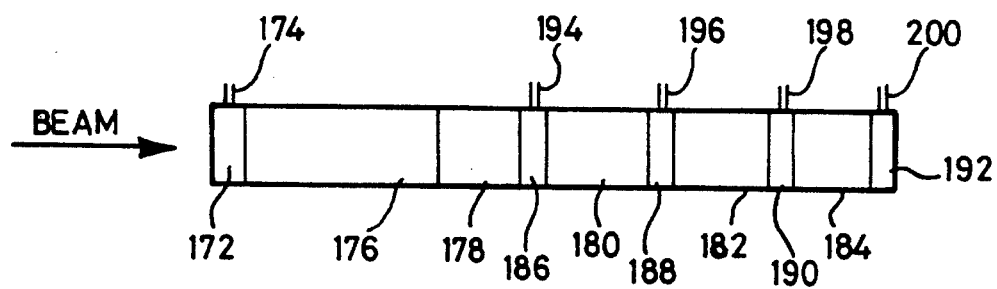

FIGS. 10a and b show a preferred method of arranging the A and B crystals so that the arrangement alternates from one layer to the next, thereby reducing cross-talk between the target/converters and the crystals;

FIG. 11 shows how detector elements can be staggered so as to further increase the distance between adjoining elements and further reduce cross-talk;

FIG. 12 is a schematic of a fibre read-out and data processing system;

FIG. 13 is a schematic diagram of the items 100, 102, 104 of FIG. 12;

FIG. 14 is a schematic illustration of a cargo screening system which allows inspection about two orthogonal axes to give spatial information as well as material identification, and FIG. 15 is a top plan schematic view of an alternative detector assembly which may be used in place of the detector shown in FIG. 7.

DETAILED DESCRIPTION OF DRAWINGS

Figure 1:
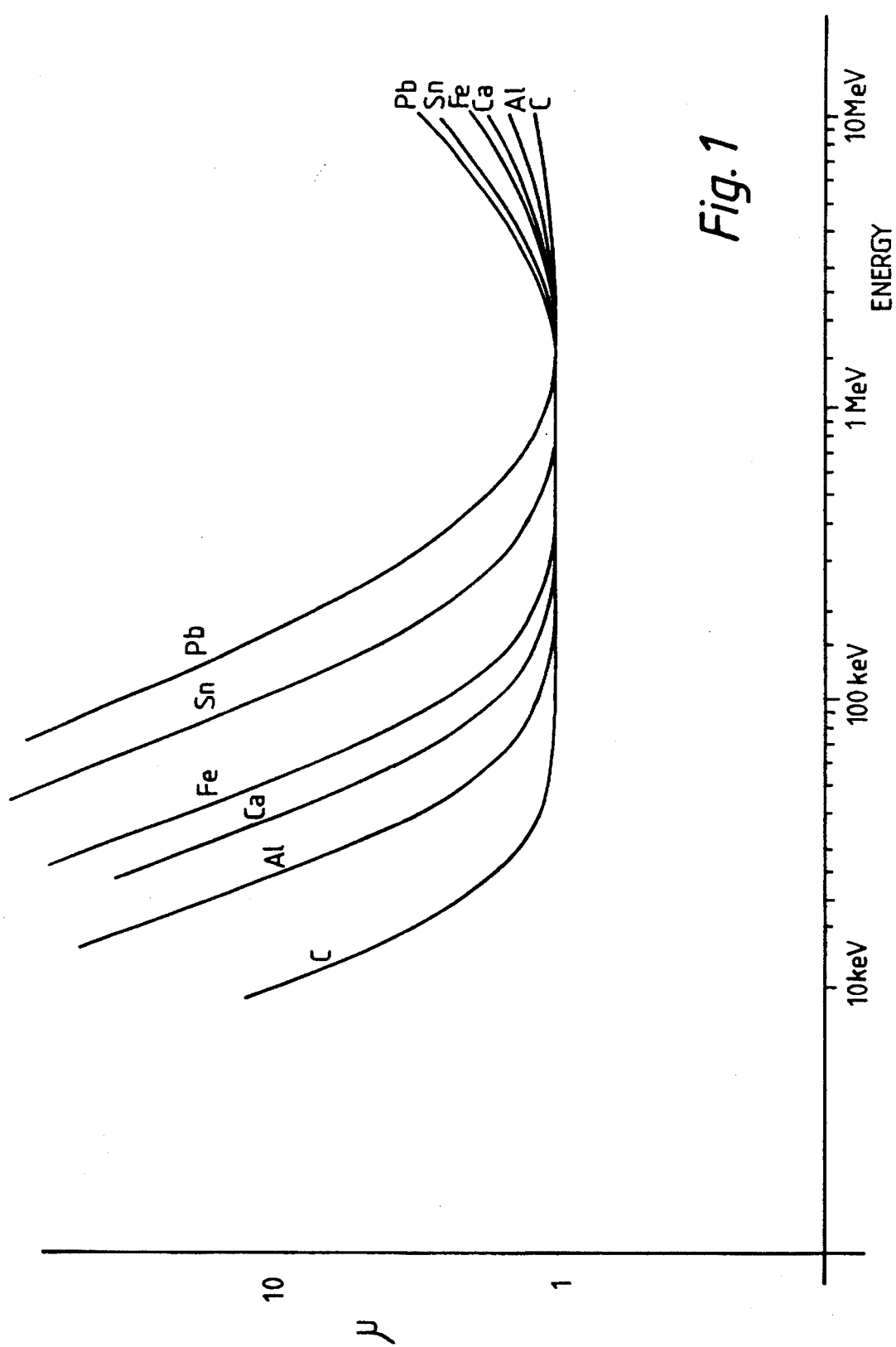
FIG. 1 is a graph showing the variation of X-ray relative transmission co-efficient with X-ray energy.

The graph of FIG. 1 shows the energy dependence of the transmission co-efficient for different materials and illustrates clearly how it is that at low electron energies in the range 10–200 KeV, good material discrimination is possible by simply determining the value of the transmission co-efficient but at higher electron energies of the order of 1 MeV and above, the divergence of the transmission co-efficient value with variation in X-ray energy is very small and certainly not large enough to be detected reliably. The lack of energy dependence at upper energy levels is well known and it is for this reason that hitherto material discrimination using high energy X-rays has been dismissed as being practically unrealisable.

Figure 2:
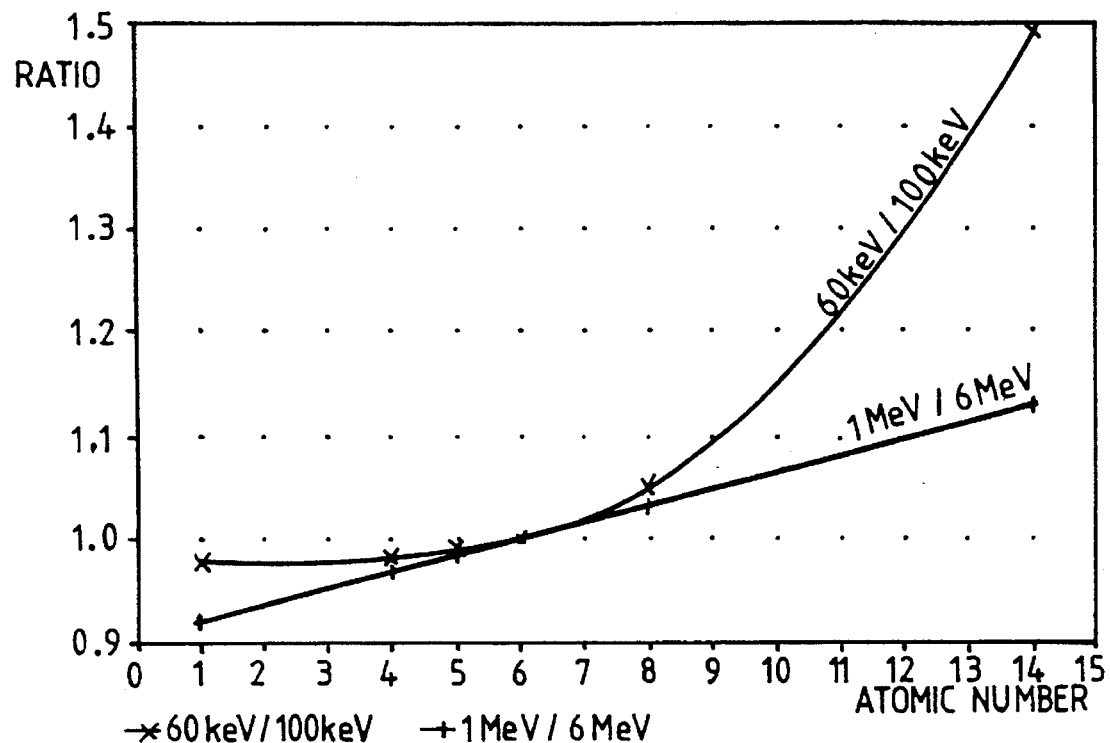
FIG. 2 is a graph showing the variation of the ratio of X-ray transmission co-efficients for materials of differing atomic number for two different low energy X-rays and two different high energy X-rays, against atomic number.

Transmission coefficients at various energies have been divided by the values at 1.5 MeV. The resultant ratio has then been divided by the ratio for hydrogen. Materials discrimination at MeV energies described here depends on the ratio of two coefficients at two different energies being different for different materials, which will only happen if the slopes of the curves shown in this Figure are different for different materials, as illustrated in FIG. 2. Note that these slopes vary at MeV energies because of the different proportions of pair production and of Compton scattering for different atomic number at a given energy.

The invention relies on the realisation by the inventors that whereas the transmission co-efficient values as between one material and another only vary over a very small range for any one electron energy X-ray, the variation of transmission co-efficient for any one material as between one electron energy and another significantly different electron energy (typically 1 MeV to 6 MeV) is quite considerable and FIG. 2 shows a plot of the ratio of transmission co-efficients as between 6 MeV and 1 MeV for different materials of atomic number in the range 1–14. The plot effectively produces a straight line the slope of which is more than adequate to enable a ratio value along one axis to be identifed against a unique atomic number on the other axis. For comparison a similar plot of X-ray energy ratios as between 60 KeV and 100 KeV for the same materials produces a curve the lower end of which is excessively flattened which prevents good discrimination between materials having an atomic number in the range 1–7. Note that for low atomic numbers (1–7) the low energy curve is much flatter that the high energy curve and so the discrimination for organic materials is compromised for low energies.

The invention thus utilises the variation of transmission co-efficient as between one energy level and another in order to distinguish between different materials at high energies, and since X-rays having such high energies can be used to penetrate considerable thicknesses of steel and like materials, the invention immediately opens up the possibility of discriminating materials inside steel containers and the like.

Figure 3:
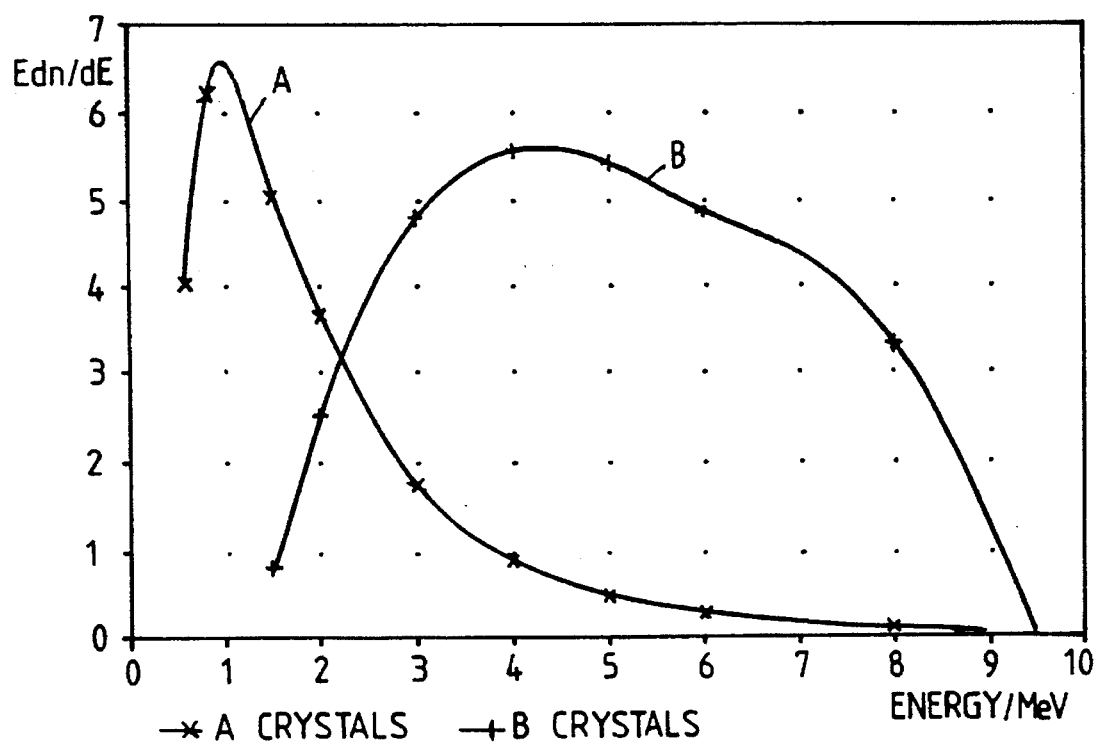
FIG. 3 is a graph in which curve A shows that part of the incident X-ray spectrum seen in a signal derived from crystal A and curve B that part of the incident X-ray spectrum seen in a signal derived from crystal B of FIG. 7 when the incident X-rays have energies in the range 1–10 MeV.

It would clearly be advantageous if a detector could be constructed which itself distinguished between relatively high energy X-rays and relatively low energy X-rays in the range 1–10 MeV and the two curves A and B of FIG. 3 indicate how, by projecting X-rays having energies in the range 1–10 MeV towards a target/converter of a dense high z material such as tungsten having two appropriately positioned zinc tungstate crystals arranged as shown in FIG. 7 a detector can be formed from such materials which if presented with a narrow window of X-rays for example in the range 1–6 MeV could be used to produce simultaneously an output indicative of the transmission co-efficient at 1 MeV and a transmission co-efficient for X-ray energies of the order of 6 MeV for any material through which the incident primary X-rays have passed. Since from FIG. 2, the atomic number is seen to be directly related to the value of the ratio of transmission co-efficients of two well separated electron energies, the mean atomic number for the material in the transmission region can be ascertained from a look-up table of ratio values against atomic number derived from the graph of FIG. 2.

It is of course not essential for the ratio to be determined simultaneously in a single detector and less complicated detectors and single energy X-ray sources can be used instead of a broad band source with more complex detector, the only requirement being that the transmission co-efficient for a particular material at one electron energy must be stored whilst the transmission co-efficient at a higher or lower electron energy is determined so that the two values are available for computing the ratio which is necessary to derive an atomic number from the look-up table.

Figure 4:
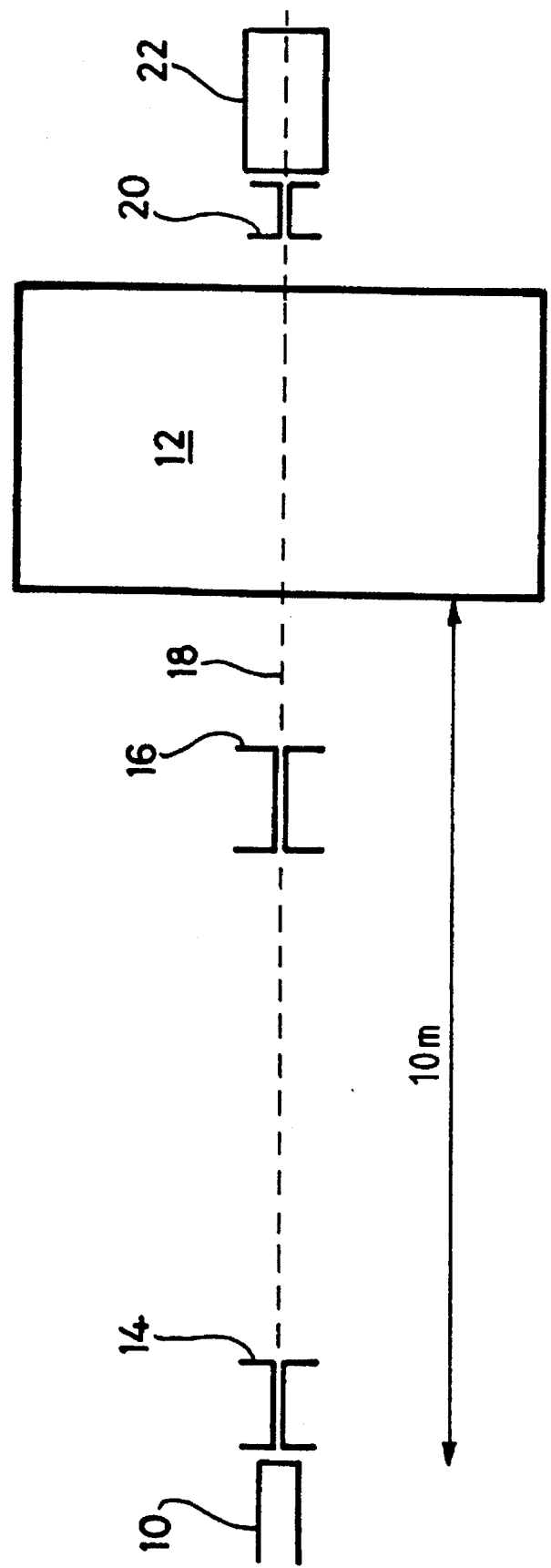
FIG. 4 is a schematic plan view of an X-ray investigation facility embodying the invention.

A simple detection system is shown in FIG. 4 in which a linear accelerator 10 producing high energy X-rays in the range 1–10 MeV is located at a distance from a testing station 12 in which an object is to be located for analysis. At least one and preferably two collimators 14 and 16 are provided between the linear accelerator 10 and the testing station 12 so that a very well defined beam of X-rays 18 is incident on an object at the testing station 12 so that the area of the object through which the incident X-rays must pass can itself be well defined. Depending on the requirements, the beam 18 may be a pencil beam or a fan having for example a very narrow dimension parallel to the page but diverging perpendicular to the plane of the page.

The area of cross-section of the beam will be tested and on the other side of the testing station is located an aligned collimator 20 and behind that a detector 22 adapted to generate photons of light or electrical current pulses when X-ray photons are received thereby. The collimator 20 ensures that only on axis X-rays which have been transmitted through the material at the testing station 12 are received by the detector 22, and in this way the signal from the detector whether optical or electrical can be callibrated to indicate the relative opacity of the material to X-rays of the known energy from the linear accelerator 10.

In order to obtain the desired ratio, the linear accelerator must be altered or changed so as to generate X-rays having for example an energy of 1 MeV for a first reading and then an energy of say 5 MeV for a second reading.

By moving the object relative to a pencil beam 18, after each pair of readings have been taken, and by computing and storing the value of the ratio of the detector readings for each relative position of the object under test relative to the beam 18, so a transmission co-efficient profile of the object can be generated and displayed and printed out or otherwise made available. In the case of a homogeneous material, the ratio should be the same for each pair of readings at each position of the beam whereas if the object contains regions of different atomic number material, the transmission co-efficient ratios will vary from one position to another and the presence and relative position of differing atomic number materials in the object can be determined from the ratio map produced from the scanning.

An investigation technique based on such a simple apparatus is time consuming and not appropriate to container inspection.

Figure 5:
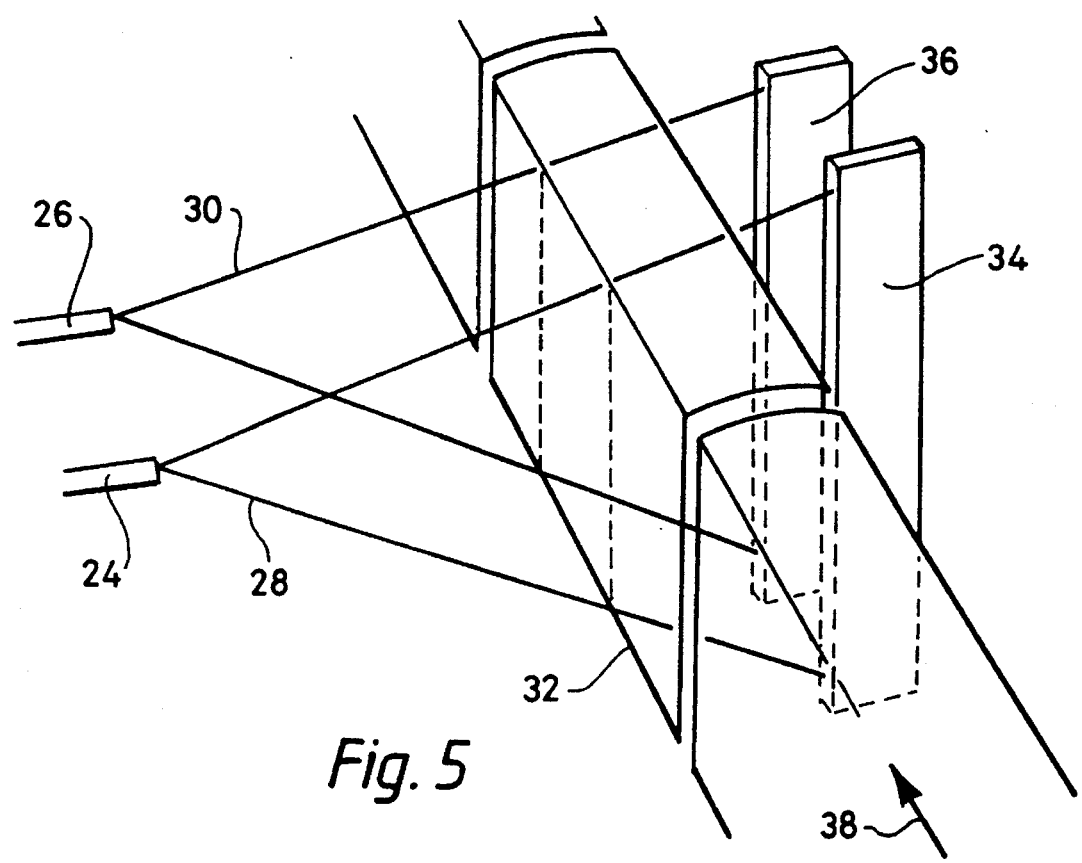
FIG. 5 is a schematic perspective view of an X-ray investigation facility using two X-ray sources and two sets of detectors.

A modification of the simple idea embodied in FIG. 4 is shown in FIG. 5 in which two such systems are located side by side but separated by a distance sufficient to prevent cross-talk. One system incorporates a linear accelerator 24 producing X-rays at 10 MeV energy and the other system includes a linear accelerator 26 arranged to produce lower energy (2 MeV) X-rays. Collimators (not shown) form the outputs into two fans 28 and 30 respectively which at a distance of some meters from the accelerators 24 and 26 have diverged sufficiently to encompass the height of a typical shipping container shown at 32.

Beyond the container two arrays of crystal detectors 34 and 36 beyond further collimators (if required) with the original collimators and linear accelerators 24 and 26 respectively so that any X-rays passing through the container 32 are received by the crystal array 34 on the one hand and 36 on the other.

By providing a large number of crystals in each array one above the other in the form of a stack, and separately addressing each of the crystals in each of the arrays, so a transmission co-efficient profile for each slice seen by each beam can be compiled and either a mean value selected from the range of signals from the crystal in each column 34, 36 or a separate value for each crystal retained where a more detailed analysis of the container contents is required.

By moving the container 32 in the direction of the arrow 38 at constant speed, the region of the container sliced by the beam 28 will eventually align with the beam 30. By storing the transmission co-efficient values from the crystal array 34 and comparing these with the transmission co-efficient values from the crystal array 36 at the appropriate future instant in time, so a ratio of transmission co-efficient values for the slice through the container can be obtained and stored, or used to produce a mean atomic number profile or snap for display or storage or other processing.

Where the container 32 is part of a train of containers, it will be seen that each container will be inspected in turn as it passes through the pair of X-ray beams and provided the X-ray energy received by the crystal arrays 34 and 36 is sufficient to provide almost instantaneous signals, relatively rapid movement of the containers past the scanning beams can be achieved.

Calibration of such a system is readily achieved by locating the same homogeneous object first in one beam 28 and then in the other beam 30 and noting the values from the crystal detectors 34 and 36 when the material is in place and providing a second look-up table for each of the crystals in each of the arrays (or where a mean value is sufficient, a mean value look-up table using the mean value from all of the crystals in the array), for adjusting the values from the first look-up table to give a uniform correct transmission co-efficient reading from each crystal for the given material. Since the second look-up table should represent constant values for each of the crystals or crystal arrays, the second look-up table values may be incorporated into the first mentioned look-up table by adjusting the atomic number values in the first look-up table so that the corrected atomic numbers are read out therefrom.

Calibration may be performed on a once off basis at installation or frequently and regularly during use such as at the beginning of each week or day of use of the facility.

Zinc tungstate may be used as the crystalline material in the arrays 34 and 36. In this event photons of light will be emitted by the crystals proportional to the X-ray energies and in this event the light must be converted to electrical energy if electrical signals are required (as will normally be the case) using photo-diodes or CCD devices or the like. In order to simplify mapping and transmission co-efficient value production in a preferred arrangement each crystal in each array may be connected to a unique position on the face plate of a CCD array by means of a fibre optic light guide so that scanning of the CCD array enables the light output (and therefore X-ray incident on each of the crystals in each of the arrays) to be ascertained independently of the other crystals in the array for storage and subsequent computation and processing.

Such an arrangement is described in greater detail in relation to later embodiments of the invention.

Figure 6:
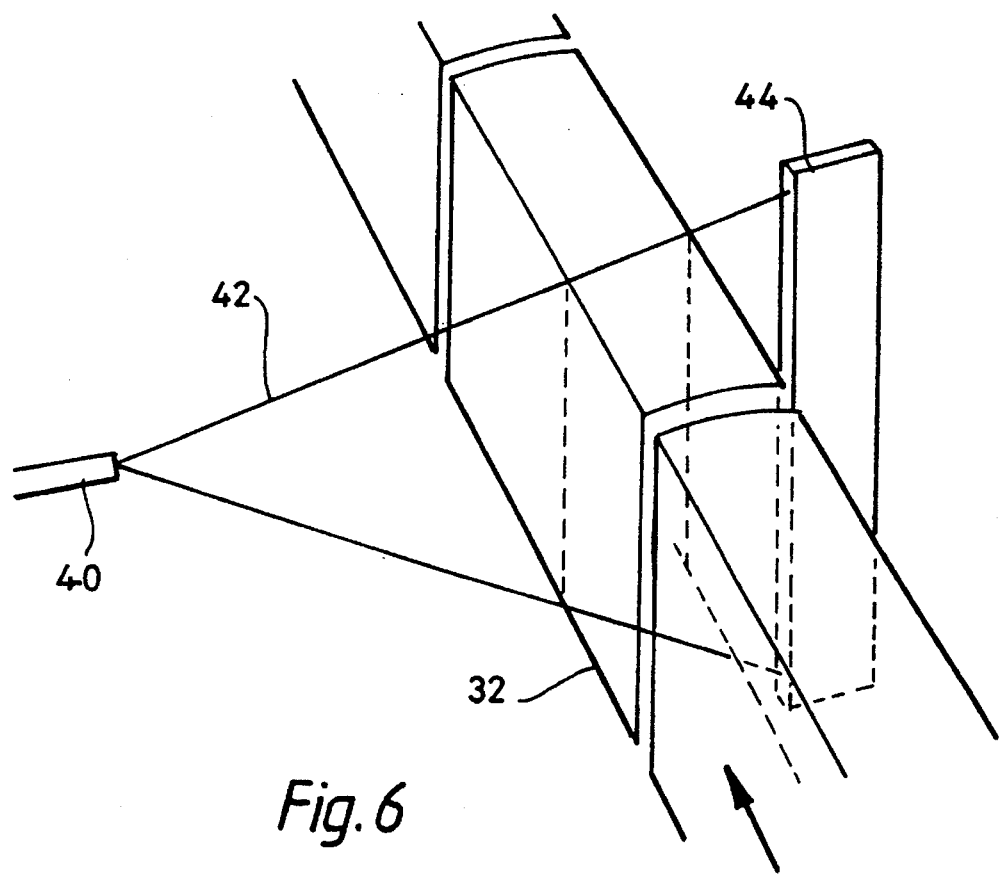
FIG. 6 is a perspective view of an X-ray facility which includes a single source and a column of detectors.

FIG. 6 is a similar perspective view to that shown in

FIG. 5 of a more preferred arrangement in which a single broad band linear accelerator X-ray source 40 produces X-rays in the range 1–10 MeV and as previously mentioned collimators (not shown) are used to form a narrow fan beam of X-ray 42 which if the linear accelerator 40 is spaced some meters from a shipping container such as 32, will embrace the full height of the container. Beyond the container is located an additional collimator (not shown) and a tall column of detector elements 44 each of which is adapted to respond separately to low energy electrons and high energy electrons (typically 1 MeV and 5 MeV respectively) transmitted by the container 32, to produce two separate outputs one corresponding to the quantity of X-rays of the lower energy and the other the quantity of X-rays of the higher energy received by the detector.

Each of the detectors is made up of a target typically of tungsten (although any other dense high z material may be used) with two zinc tungstate crystals located on opposite sides thereof and positioned so as to receive photons of energy produced on the one hand predominately by electron-positron pair production and on the other hand predominently by Compton scattering. In order to cut out the Compton scattered energy, a filter such as a lead absorbing plate may be located between the target and the zinc tungstate crystal located to receive the energy produced by electron-positron pair production since the energy level of the latter is considerably greater than the energy level of Compton scatter produced photons and a lead plate will absorb the lower energy photons and transmit only the higher energy photons thereby ensuring that the second zinc tungstate detector only tends to receive energy attributable to electron-positron pair production and virtually none resulting from Compton scatter.

In FIG. 7 a tungsten target 46 has incident thereon X-rays 48 after passing through a shipping container such as 32, and forwardly directed Compton scattered X-rays in a band of 30° to 60° from the axis of the incident X-ray are detected by a zinc tungstate crystal 50 whilst annihilation X-rays produced by electron-positron pair production and propagating in a generally rearward direction are received by a second zinc tungstate crystal 52 located on the other side of the target 46. Between the target and the second crystal is located a lead absorbing plate 54 to further reduce the Compton scatter X-rays incident on the second crystal.

Both crystals scintillate when X-rays are incident thereon and light photons produced thereby are conveyed via fibre optic light guides 56 and 58 to separate regions of two separate CCD scanning devices (to be described in more detail later but substantially as described in UK Patent Specification No. 2204770) so that not only are the two transmission co-efficient values for the high and low energy X-rays available simultaneously to enable a ratio of the two values to be obtained, but the two values obtained from each of the detectors in the stack can also be distinguished from the two values produced by all of the other detectors in the stack during each scan. In this way the mean atomic number profile of the whole height of the slice through the shipping container 32 can be obtained by scanning the two CCD arrays.

Figure 8:
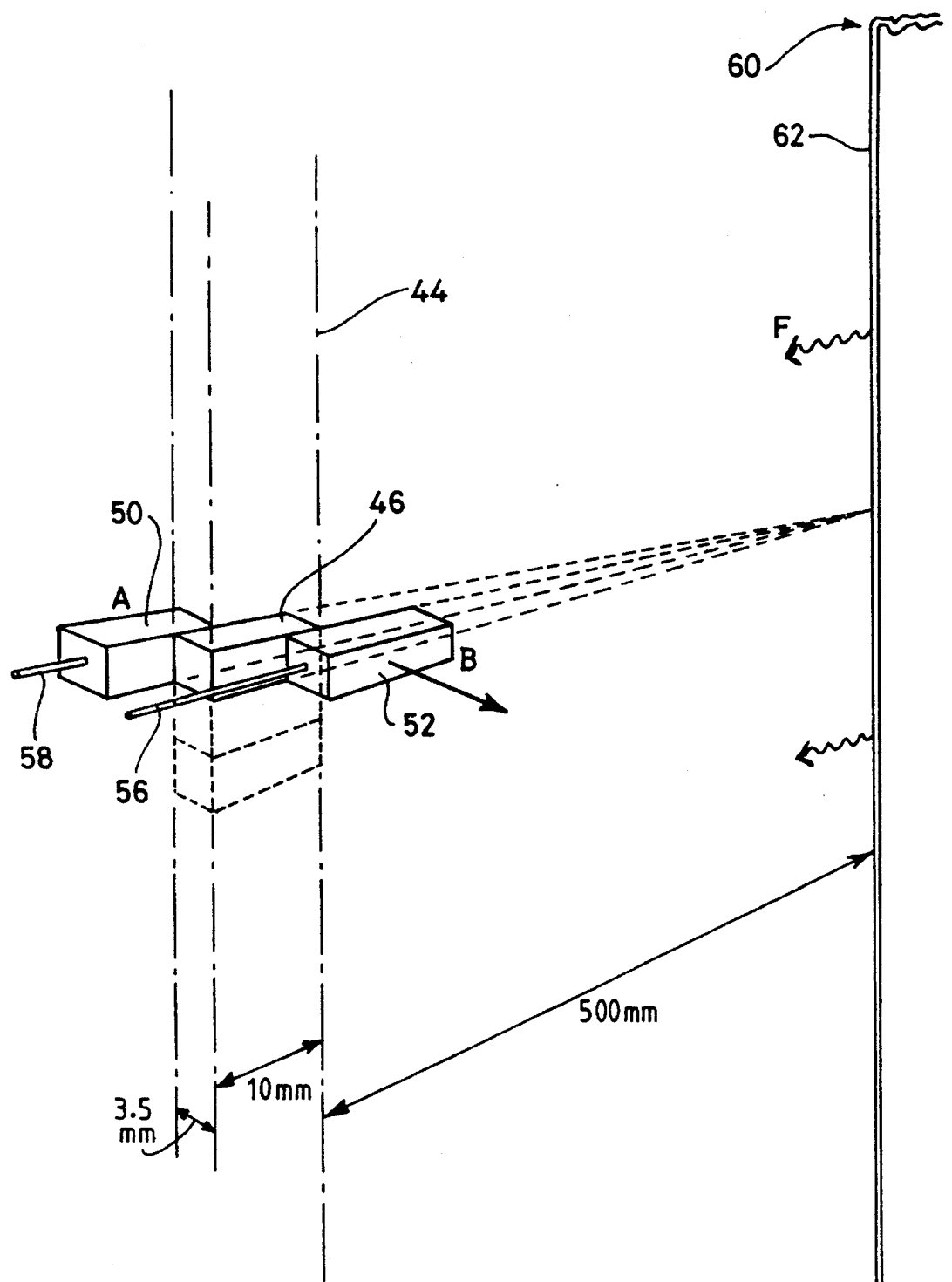
FIG. 8 is a schematic perspective view showing how the target/convertor and crystals are mounted in relation to one another and the collimator.

FIG. 8 shows diagrammatically an arrangement of target and crystals in relation to a collimator. The collimator in question corresponds to item 20 in FIG. 4 in that it is the collimator between the object under investigation and the detector. In FIG. 8 the collimator is identified by reference numeral 60 and is shown as defining a narrow vertical slit 62 through which X-rays can pass. The detector elements in the column 44 are arranged approximately 500 mm from the exit slit 62 of the collimator 60 with the target elements 46 located on the axis of the collimator and the crystals 50 and 52 located on opposite sides. Fibre optic light guides 58 and 56 are shown leading away from the rear of each of the crystals but the lead absorber plate 54 is not shown in FIG. 8.

By arranging similar detector assemblies at intervals above and below that shown, a complete array of detectors can be built up.

Since the fan of X-rays exiting from the collimator slit 62 is diverging at least in the vertical plane, the column array may be replaced by an arcuate array so as to keep the mean distance between the source of the fan and each of the detectors substantially constant. However in view of the distances involved (typically in excess of 10 meters between the linear accelerator and the detectors) and the height of the shipping container which is only some two or three meters at the most, the angles involved are very small and the errors introduced by a straight line column of detectors as opposed to an arc may in practice be so small that it can be ignored or calibrated out.

Although the central element of each detector unit is referred to as a target, sometimes these items are referred to as convertors since they serve to convert X-rays emanating from the slit into secondary X-rays emanating from the block 46.

Figure 9:
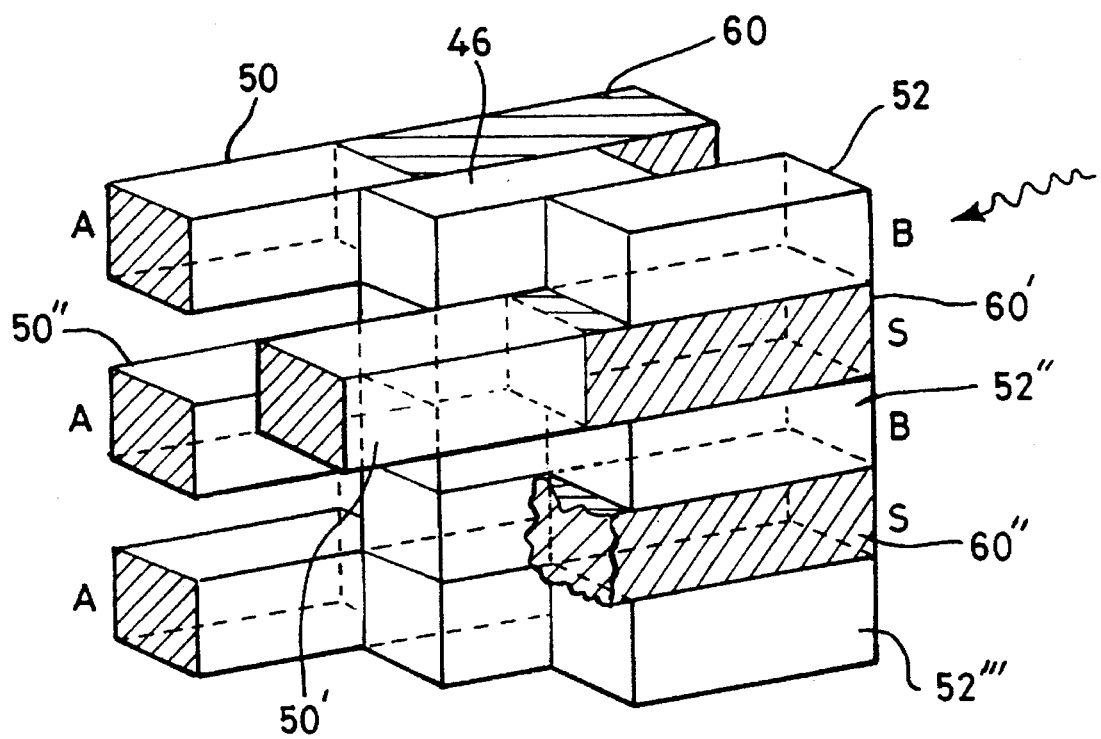
FIG. 9 shows how a stack of detector elements can be arranged with intermediate shielding.

As shown considerable cross-talk will result between adjoining detectors in the column unless steps are taken to separate the detectors by a sufficient distance and/or employ appropriate screening. With this in mind an alternative arrangement is envisaged shown in FIGS. 9 and 10 in which the crystals are alternately positioned on opposite sides of the target converter elements 46. Such an arrangement is shown in FIG. 9 in which in the top layer shown the target 46 is flanked on the left hand side by a crystal 50 and on its right hand side by a crystal 52.

On the layer below the two crystals are reversed and crystal 50' is shown on the right hand side and the B crystal (52') (not visible) occupies the mirror image of the position of crystal 52, albeit one layer below. On the next layer down, the crystals are arranged in the same way as on the top layer so that 52'' is on the right hand side and 50'' lies on the left hand side. The crystals 50, 50' etc are A type crystals in that they respond to Compton scatter X-rays and the crystals 52, 52' etc are B type crystals in that they respond to annihilation X-rays produced by electron-positron pairing. By staggering the crystals so that they appear first on one side and then on the other in successive layers, so considerable spacing is introduced between crystals in adjoining layers. Cross-talk between a crystal 52 and for example the next crystal below it 52'', can be reduced by inserting a layer of screening material such as lead 60 is fitted between the two crystals 52 and 52''. Typically the lead shield 60 extends to the front of crystal 50' and is of similar cross-section.

A similar sandwich of lead 60'' is provided between crystal 52'' and 52'''. The crystal 50''' which extends to the rear of shielding element 60' is not shown for clarity.

Fibre optic light guides such as 56 and 58 extend from the crystals in the same way as before since the lead shielding does not obscure a rearward facing face of any of the crystals. Again for clarity all such optical connections have been omitted from FIG. 9. As shown in FIG. 7 the optical fibres may be connected to the crystals by optical elements for example of perspex which may taper from the crystal size to the fibre size.

Figure 10B:
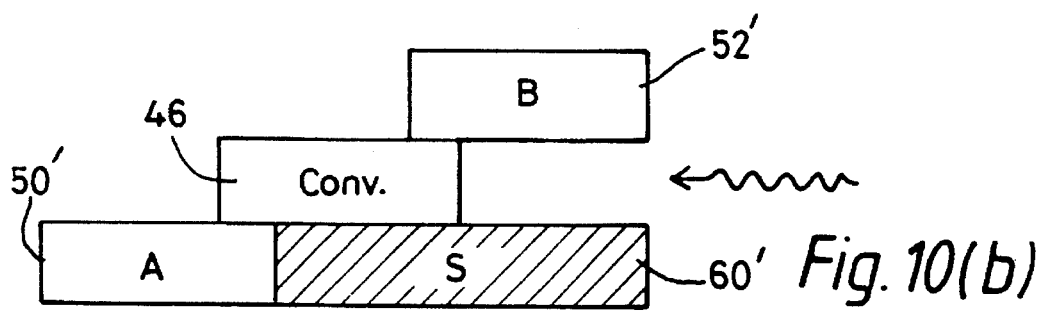

FIG. 10 shows the plan views of two adjacent layers of the detector assembly of FIG. 9 showing how the shielding occupies first one side and then the other of the array. Thus in FIG. 10a, crystal 50 is shown in alignment with a shielding member 60 and on the other side of the convertor 46 is located the rearwardly positioned crystal 52. On the next layer down the converter 46' remains in the same position but the other elements are transposed so that the crystal 52' occupies the side previously occupied by items 50 and 60 and crystal 50' and shielding 60' occupy the other side of the converter 40'.

Additional screening may be provided by lead sheeting or the like horizontally sandwiched between the adjoining detectors.

In an attempt to obviate all the need for lead screening which adds to cost and weight, the detectors may be arranged in a form of staircase so that each detector is above and to the rear of the one below in a succession of five steps after which the arrangement is repeated. It has been found that by separating crystals and converters based on centre line measurement by approximately 100 mm, cross-talk between adjoining converters and crystals and between adjoining crystals can be reduced to one part in one thousand or less and this is generally an acceptable level of cross-talk for most purposes. By ensuring that 100 mm vertically between detectors and horizontally between one detector and the next in each five step staircase, so the minimum distance between any elements in adjoining detectors is of the order of 100 mm and cross-talk can be reduced to an acceptable level. The dimensions mentioned apply to crystal converter arrangements in which the converter is of the order of 10 mm axial extent and the crystals on either side are similarly dimensioned in axial extent and the height of each crystal and converter is of the order of 3.5 mm. Such an arrangement is shown in FIG. 11 in which the first detector in a first staircase is referenced 62, the next 64, the next 66, the next 68 and the last 70. In the staircase immediately thereabove the first detector element is referenced 72, and the remaining elements 74 to 80 respectively. X-rays emanating from the detector collimator are assumed to be travelling from right to left 82.

FIG. 12 shows how fibre optic light guides from the arrays of crystals can be collected together to be read by CCD imaging devices. To this end one each of fibres 56 and 58 of FIG. 8 are shown terminating in a demagnifying taper of optical material 84 (in the case of fibre 56) and 86 (in the case of fibre 58). Other fibres also from B type crystals terminate in the end face of the demagnifying taper 84 and other fibres from A type crystals such as crystal 50 in FIG. 8 terminate in the face of demagnifying taper 86.

The position of each optical fibre is fixed in space and in relation to the other terminating optical fibres so that the pulse of light on any one optical fibre will produce a small pin point of light at some point in the area of the demagnifying taper to which the relevant optical fibre extends and by scanning the whole area very rapidly so all of the scintillation light can be detected and a video-like signal produced indicating the X-ray transmission co-efficient profile for the slice being scanned.

Each of the tapers 84 and 86 may be extended by means of an intensifier stage 88 and 90 respectively to terminate at a CCD camera 92 and 94 respectively. Typically a 200 Hz or 1000 Hz frame rate is employed.

A master clock generator 96 provides timing pulses from which addressing of the CCD array is achieved both on a line and frame basis and typically each line is divided into discrete intervals typically referred to as pixels the position of each pixel corresponding to the position of one of the optical fibres such as 56 in the scanning of the reduced area face plate produced by the taper 84.

The signal obtained by scanning the CCD array in each case is supplied a signal path 96, 98 respectively to each of two data processing systems 100 and 102 respectively by which the data is analysed and processed to produce ratios, atomic numbers and the like.

The two trains of data so produced are supplied to a data consolidation and presentation computer 104 one output of which supplies an alarm signal is generated via path 106 to an alarm 108 whilst the other data path 110 supplies a number of separate terminals or viewing stations of which three are shown by way of example at 112, 114 and 116. Using an appropriate networking arrangement and appropriate multiplexing, the visual displays such as 112 etc can be raised to show either separate parts of a complete container or other device which is being tested so that when all of the screens are viewed the whole of the scanned container can be seen or each screen can have presented thereon the outline of each of a succession of containers which are passing through a testing station thereby giving each operator a reasonable period of time to study the whole of one container. Inside each container outline the computer is arranged to display as by mapping and differential colouring or shading, different material atomic numbers to enable the material in each container to be analysed visually as well as automatically checked by the computer.

An alarm condition may for example be predetermined as existing if material of one mean atomic number is found to form part of an overall container which includes within its map material of at least one other predetermined mean atomic number. Thus for example an alarm signal may be generated by a computer 104 if material having a mean atomic weight corresponding to the predominent material in an electric storage battery is found in close association with the mean atomic weight of material known to be explosive.

Although not shown means is provided for tagging the container as by a visible marking to indicate that X-ray scanning thereof has produced an alarm signal.

FIG. 13 is a block schematic diagram of the signal processing stages of items 100 and 102 in FIG. 12 and the data processing and computation stage 104 of FIG. 12. Those elements making up each of the items of FIG. 12 are contained in outline boxes appropriately labelled with the corresponding reference numeral from FIG. 12 for ease of reference.

The content and operation of the items 100 and 102 is similar and to this end the operation in item 100 only will be described in detail.

The video signal from the CCD scanner 92 is supplied on line 118 to a flash ADC device 120. Synchronisation and timing pulses from the clock 96 are supplied along line 122 to synchronise the flash ADC device 120 and are also supplied to a memory 124 containing a pixel to optical fibre map for generating appropriate addressing information to be linked with the data received from the CCD so that digital data relating to different pixels in the CCD array and generated by the ADC unit 120 can be routed to appropriate areas of a large random access memory (RAM) 126. The digital data supplied to RAM 126 passes through a summation unit 128 to which data from the RAM 126 is fed back via feedback path 130 to enable total light yield for each fibre to be accummulated. The need for the summation arises from the fact that the pixels may be much smaller than the cross-section of the optical fibres viewed by the CCD and in order to obtain a digital value of the total light received from any one fibre, so a number of pixels need to be addressed and the digital data arising therefrom accummulated into a single larger number. The feedback loop 130 and summation unit 128 achieve this.

After a complete scan, the data in each of the areas in the RAM 126 comprise the digital value of the light received from the optical fibre relating to the area of the RAM. Insofar as the CCD array can be thought of as dividing the image supplied thereto in a large number of pixels, the RAM 126 can be thought of as being divided into a large number of dexels each dexel corresponding to the data arising from a group of pixels within the original CCD array which in turn relate to the area of the CCD affected by one of the optical fibres leading thereto.

The data stored in each dexel can be read out by appropriate addressing via a calibration stage 132 containing a plurality of algorithms typically one for each dexel and each preset during an initial calibration of the apparatus so as to normalise the digital value stored in each dexel by setting interpolation co-efficients for each dexel. The signal delivered along line 134 thus comprises a corrected or normalised digital value for each of the dexels in RAM 126.

As previously mentioned an exactly similar arrangement is contained within item 102 so that the data along line 136 also corresponds to normalised digital values of the light received from the optical fibres from the other series of crystals associated with the detectors. Thus if the data along line 118 is derived from CCDs fed with light from A type crystals (see earlier description) then the signals along line 138 comprise the electrical signals from the CCD supplied with light from fibres from the B type crystals.

The two digital data streams on 134 and 136 are supplied synchronously to a comparator 140 so that digital data relating to the A crystal out for one detector arrives at the same time as the digital data relating to the B crystal of the same detector thereby enabling the comparator 140 to generate a ratio of one digital value to the other characterising the material through which the original X-ray beam has passed. This is achieved by using a look-up table in item 142 comprising a RAM or ROM in which digital values are stored corresponding to mean atomic numbers and linked thereto to digital value corresponding to ratios of transmission co-efficients for materials having such mean atomic number so that the nearest mean atomic number can be read out along line 144 in response to an appropriate ratio value supplied from the comparator 140 along line 146. The mean atomic number may be displayed either as a number or in addition or alternatively the name of the material having that atomic number. The data on line 144 corresponds to the data along line 106 of FIG. 12 and it would be appreciated that a warning system which may itself include a computer may be linked to the datablock 144 to generate appropriate warning signals in the event that particular mean atomic numbers are identified.

The digital data streams on 134 and 136 can be thought of as video signals since each digital value corresponds to a particular dexel within the associated RAM 126 and if the digital signals are supplied to the unit 140 at a high enough rate (as would normally be the case) the series of ratio values can be thought of as comprising a video signal which if the storage and addressing of dexels in the RAMs 126 is mapped accurately relative to the optical fibres supplying the CCD rays, timing signals derived from the master clock 96 can be used to control the scanning of a visual display unit such as a CRT to which the varying ratio value signals from item 140 can be supplied as beam controlling signals for controlling either the grey level or the colour produced by the visual display unit so that a grey level display or coloured display can be obtained corresponding to variation of mean atomic number, the position of each such atomic number signal in the display corresponding to the position in the original container of the material giving rise to that particular atomic number value. In this way a visual picture of the container or part of the container depending on the scale, can be built up on a television screen as the container passes through the X-ray scanning system. Conversion to grey level may for example be undertaken in unit 148 whereas the generation of colour signals from the digital data may be generated in item 150.

In addition to displaying details of the mean atomic number of materials inspected by the X-ray scanning station, data processing can be applied to the video signals from 148 or 150 or both by a computer 152 programmed to recognise potentially threatening shapes and combinations of different materials (by recognising different mean atomic numbers) and in particular programmed to look for nitrogen rich materials and the presence of lead. The former is typical of the signature of an explosive material whereas the detection of lead may indicate the presence of a detonator.

Depending on the size of the computer 152 it is also possible to compare the ascertained contents with cargo manifests and the like. To this end data from a memory 154 may be called on by the computer 152 for comparison purposes, the data in memory 154 having been input in any convenient manner as by scanning or monitoring by a keyboard or the like from information contained on cargo manifests, accompanying documentation and the like. To this end the input is shown diagrammatically at 156.

The computer 152 may include or be associated with a large memory into which a record of the perceived contents of each container can be stored together with an identifying number or flag relating to the identification data on the manifest so that should there be a requirement to trace the origins of any particular container as a result of a subsequent incident, it can be done readily and quickly using the stored data.

Where it is desired to eliminate data relating to known cargo containers, railway waggons and the like, the memory 154 can also contain data relating to scanned images of such containers, waggons and the like which can be called up and subtracted from the data derived from the scanned container or waggon so that the resulting data relates solely to the contents of the container and not to the material from which the container is constructed.

A computer 152 may also be used to control one or more image displays. In the simplest case a single large screen monitor may be provided supplied with signals along line 158 from the computer 152, the data corresponding to the whole of each container which has been scanned so as to indicate in the display the perceived contents of the container based on mean atomic number. Alternatively a plurality of visual display units such as CRTs may be controlled each one being supplied with part of the overall picture signal so that each of the displays reveals the perceived contents of a unique part of this container which has been scanned. In this arrangement although each of the displays only shows part of the container, the whole of the container can of course be seen by inspecting all of the displays and in a typical set up, an operator would be positioned in front of each of the displays so that as a container is displayed in part on their screen, they are able to examine the part shown to them and make a note of what is seen. Each operator may for example have available to them a panic button by which they can alert the whole operation to the fact that they are seeing something of concern on the screen in front of them which in turn will automatically flag the container concerned and enable the lorry or train carrying the container to be diverted to a safe place.

Since automatic flagging and relating manifests to containers and the like is required, any such warning signals generated by the operator is preferably routed via computer 12 so that signals generating alarms, railway signalling, points control and road diversion can be generated and sent via a path such as 160 to the relevant equipment and apparatus.

The computer 152 may also generate archive material for customs and other long term record keeping such as electrical and/or optical data which may be stored either on magnetic disc or optical storage media so that a complete record of each container scanned and processed by the facility can be maintained for subsequent checking.

The memories 126 and the computer 152 require to be reset periodically to indicate that incoming data relates to a fresh container or waggon. To this end a reset signal is shown supplied to each of these items to enable the appropriate reset command to be given. The reset signal may be generated electro-mechanically or electro-optically using appropriate sensors or in any other convenient manner to generate an appropriate signal indicating that one container has passed through the scanning station and another is about to enter it.

It is to be understood that the schematic diagram of FIG. 13 and the earlier diagram of FIG. 12 is not intended to be an exhaustive description of a data processing system and buffers, timing circuits, control circuits, power supplies and the like have been omitted for clarity.

So far the apparatus illustrated in the drawings has been intended for scanning a container in two dimensions only. Thus a container may be viewed from above or from below or from one side or the other.

Considerably more information can be obtained if a container is scanned from two directions simultaneously and the data combined by way of appropriate data processing apparatus so that a thee-dimensional image of the contents of the container can be built up based on mean atomic number. To this end two systems such as described in relation to FIGS. 12 and 13 can be arranged one system inspecting a container from a horizontal viewpoint and the other from a vertical viewpoint. Such an arrangement is shown in FIG. 14. Here a first system containing a linear accelerator 162 and a detector array 164 enables information relating to vertical slices viewed from the side to be determined and a second system containing a linear accelerator 166 and detector array 168 serve to simultaneously scan the object 170 from a vertical position above the container. To this end the detector array 168 is located below the path along which the object 170 moves through the inspection station.

The signals from the second detector array 168 are treated in exactly the same way as the signals from the detector array 164 so that duplication of the systems shown in FIGS. 12 and 13 is required except that after formation of the ratio signal in each of the two parallel systems, the signals may be merged or combined or otherwise made available simultaneously to allow a more powerful computer in place of the computer 152, to handle the data and enable images to be presented on appropriate displays of either two-dimensional views of the contents viewed from the side or above or another two-dimensional view from end on showing the position of distinguishable different materials within the container through its cross-section or three-dimension displays may be produced which enable not only the cross-section but also the lengthwise position and extent of material differences within the container to be evaluated at a glance. The dexel information so displayed will be of a relatively coarse definition, it can be small enough to enable the shapes of certain objects to be readily recognised and this in combination with a knowledge of their mean atomic number will readily allow suspect objects to be either eliminated or flagged for further inspection.

FIG. 15 illustrates an alternative composite detector.

Item 172 comprises a scintillation crystal with optical fibre read-out via 174. Item 176 comprises a beam hardener of low z. Items 178, 180, 182, 184 comprise high z converters and items 186, 188, 190, 192 comprise further scintillating crystals with optical fibre read-outs 194, 196, 198, 200. Light from 200 indicates an incidence of very high energy X-rays on 172 whereas light from 194 but not from 196 etc indicates only low energy incident X-rays on 172.

We claim:

1. A method of detecting the mean atomic number of a mass of material within a container comprising the steps of:
   (a) subjecting the material to high energy X-rays and determining the mean number $N_A$ of X-rays transmitted through a region thereof,
   (b) separately and simultaneously subjecting the same region of the material to X-rays having a significantly higher energy than the first mentioned X-rays and determining the mean number $N_B$ of the higher energy X-rays transmitted therethrough,
   (c) computing the value of the ratio $N_A$ to $N_B$, and
   (d) determining from a look-up table and delivering as an output the average atomic number corresponding to the computed value of the $N_A/N_B$ ratio.

2. A method according to claim 1 in which separate X-ray sources and X-ray detectors are employed, spaced apart so as to reduce cross-talk and interaction therebetween, and either one or both of the values of $N_A$ (obtained from the source detector combination operating at the lower energy level) and $N_B$ (obtained from the source detector combination operating at the higher energy level), is/are stored as appropriate to be available for the ratio computation step.

3. A method according to claim 1 in which a single broad energy band X-ray source is employed to project a range of high energy X-rays of 1 MeV and above towards the material (e.g. the container).

4. A method according to claim 3 in which a composite detector is placed beyond the material which, on bombardment by transmitted X-rays produces substantially simultaneously a first component predominantly attributable to the higher energy component of the incident X-rays, and a second component predominantly attributable to the lower energy component of the incident X-rays; the energies carried by the said two components is determined; numerical values relating thereto are generated; a ratio is computed of one numerical value relative to the other; and, using a look-up table as aforesaid, the mean atomic number for the material through which the X-rays have passed is derived therefrom, using the value of the said ratio.

5. A method according to claim 4 in which the products of Compton scattering in the target/convertor in the composite detector and electron-positron pair production are preferentially detected in separate crystals.

6. A method according to claim 4 in which photons attributable to higher energy X-rays transmitted through the material are preferentially detected by detecting rearwardly propagated annihilation photons attributable to electron-positron pair production in the target, typically at an angle of 135° and greater.

7. A method according to claim 5 in which the preferential detection is enhanced by removing lower energy photons from the rearwardly propagating photons by filtering, as by using a sheet of lead or tungsten or like material, and forcing all the rearwardly propagating photons to pass therethrough, so that only the higher energy photons reach the second detector.

8. Apparatus for performing the method according to claim 5 comprising an x-ray source, a target/convertor, typically of tungsten, and two crystals located so as to separately receive forwardly propagating photons in the range 30° to 60° off the axis and to receive rearwardly propagating photons in the range 135° to 180° off the axis.

9. Apparatus for performing the method according to claim 1, comprising an x-ray source and a sandwich of absorbers and scintillators enabling an electromagnetic cascade to be sampled at depths from the end of the sandwich on which X-rays are incident.

10. Apparatus according to claim 9 in which the first element on which the X-ray beams impinges comprises a relatively thin crystal, so that the energy deposited is more or less independent of X-ray energy and the spectrum of sampled X-rays is therefore strongly peaked around 1 MeV, and the thin crystal is followed by a low-z beam hardener which preferentially removes lower energy X-rays from the beam, which is then transmitted to a series of high-z converters (which favour pair production) which alternate with and are thereby sandwiched by thin crystals which sample the electrons produced by collisions upstream of the crystals.

11. Apparatus according to claim 10 in which light from the crystals is conveyed to a photo-electric device using optical fibres.

12. Apparatus according to claim 10 in which the outputs from all the crystals are optically coupled to give a single optical output to the photo-electric device.

13. A freight checking facility incorporating at least one X-ray source/detector combination as claimed in claim 9, and means for computing the ratios of detector output signals from each detector and determining the mean atomic number of the material exposed to the X-rays, and further comprising:

(a) a housing or building surrounding the X-ray source(s) and X-ray detectors for absorbing any X-rays not absorbed by the material under test or by the detectors, (b) entrance and exit doors;

(c) a path leading to the entrance, extending through the housing or building and leaving through the exit which in the housing or building extends between the source(s) and the detectors, to enable freight to move into, through and out of the housing or building;

(d) at least two paths beyond the exit with means for diverting freight which has been scanned onto one or the other of the two paths, the length of each of the two paths being such as to permit all of a group of linked items of freight to be contained wholly thereon;

(e) means by which freight from either of said two paths can be moved onto a single ongoing path beyond the section containing at least two paths; and (f) means for preventing at least one item of freight from leaving the path onto which it has been conveyed if an alarm signal gathered in response to the earlier scanning of the freight on that path;

whereby an item of freight which has to be physically checked because of what has been seen during the scanning, need not impede the ongoing progress of other items of freight which do not cause alarm signals to be generated.

14. A facility according to claim 13 further comprising a linear accelerator operating at approximately 10 MeV together with various targets and beam hardeners is a collimator to define a fan beam of small width of the order of a few millimeters, and a path such as a railway track, roadway or conveyor extending perpendicular to the axis of the beam at a distance of typically 10 meters from the source target.

15. A facility according to claim 14 and further comprising another collimator located on the other side of the path to eliminate scattered X-rays which are not within the width of the fan, and an array of converters situated beyond the second collimator, crystals and absorbers being arranged in a manner so as to reduce cross-talk between one crystal and another to a level of approximately one part in one thousand, and optical fibre means (or electrical conductor means if the crystals generate electrical signals) leading to a device by which each crystal output can be scanned in turn and a value obtained therefrom corresponding to the X-ray photon population incident on the crystal concerned.

16. A facility according to claim 13 further comprising means programmed to generate an alarm signal in the event that certain ratio values are detected (for example corresponding to drugs, explosives and the like) or certain combinations of ratio values are detected within the same freight container.

17. An x-ray analysis device for determining the mean atomic number of an object by locating a broad band X-ray source on one side of a testing station and a detector on the other side, comprising: a target having X-ray detectors positioned adjacent thereto, one of the detectors being positioned and adapted to receive X-rays scattered by the detector target in a generally rearward direction back towards the source and up to 45° off the rearward axis and the other detector being positioned and adapted to detect forwardly propagating X-rays scattered off axis typically by more than 30° and by less than 60° thereto, due to so-called Compton scatter, each of the X-ray detectors providing signals proportional to the number of X-ray photons incident thereon; means responsive to the two detector outputs forming a ratio of the number of photons detected by the two detectors and forming a numerical value thereof; a look-up table containing information pertaining to given numerical ratios for different materials; means for determining from the look-up table the information corresponding to the numerical ratio obtained from the outputs of the two detectors; and means for delivering the said information as an output signal.

18. A device according to claim 17 in which the target is formed from tungsten, and the X-ray detectors are crystals of zinc tungstate or cadmium tungstate, the X-ray photons being converted by the crystals into electromagnetic radiation in the visible range, and the photons of visible light being detected and quantified using a photo-electric sensor adapted to generate from the light emitted from the crystal an electric current which can be measured to give a numerical value proportional to the X-ray photon population incident on the appropriate crystal.

19. A device according to claim 18 in which light emitting crystals are employed, light collection means being provided to gather light emitted by each crystal, and a light guide means such as optical glass or plastic fibres, for conveying the light to an intensified CCD camera or the like.

20. A device according to claim 19 in which an intensified CCD camera is employed where the light guide means from a large number of detectors in the array terminate at differently addressable points over the surface of the CCD camera, so that very low light levels and therefore X-ray emissions are detected using the light integrating properties of such a device.

21. A device according to claim 19 further comprising means for scanning after a suitable period of time has elapsed to permit integration of photons arriving thereon.

22. A device according to claim 17 in which the X-ray source is a conventional 10 MeV electron linear accelerator with targets and beam hardeners to determine the X-ray spectrum emanating therefrom.

23. A device according to claim 17 in which the X-rays from the source are collimated into a divergent but narrow beam which can be likened to a fan extending in a generally vertical plane from the point source, and a plurality of detectors are positioned in an array in the same vertical plane on the remote side of a testing station each pointing towards the source and preferably to the point from which the fan of X-rays emanates, and each distanced therefrom by approximately the same length, the two X-ray sensitive crystals associated with each detector being separately addressable to determine the photon population seen by them, for determining the ratio as aforesaid for each detector, means being provided for memorising the ratio obtained from each detector to enable a profile to be produced of all of the ratios seen by all of the detectors in the array.

24. A device according to claim 23 in which the detectors are arranged in two or more (typically four or five) different arcs also centred on the same point (e.g. the X-ray source) but having successively increased radii of curvature, and locating adjoining detectors on different ones of the arcs.

25. A device according to claim 17 further comprising means for introducing relative movement between the analysis device and the object, generally perpendicular to the plane of the X-ray beam, so that the object can effectively be scanned from one end to the other, and means for memorising the signals obtained during the lengthwise scanning, so that a two-dimensional profile can be obtained for the whole object as viewed by the detector.

26. A device according to claim 25 in which the object is mobile and the source and the detector array are aligned and fixed in position while the object is moved steadily therebetween, the source and detector array being located either on opposite sides of the object, or above and below the object.

27. A device according to claim 17 comprising a second source/detector combination located perpendicular to the first source/detector combination, so that the narrow beam of the second source propagates through the object in the same (or a parallel) plane as that occupied by the first beam but with the central axes of the two beams at right angles.

28. A device according to claim 27 in which the first source and detector array is located on opposite sides of the testing station, the second source is located above, and the second detector array below, the testing station, so that a composite profile of the object can be obtained for each of the inspected slices, across its width, as well as from top to bottom thereof.

29. A device according to claim 28 in which the object is rectilinear and the signals corresponding to the two profiles are stored, so that they can be employed to control a visual display to allow cross-sections of the object to be displayed showing material variation therein as viewed from side to side, from top to bottom, and from end to end.

30. A device according to claim 28 in which the signals are combined to permit a series of three-dimensional isometric views of the object to be displayed, with the nearside end face in each object corresponding to the cross-section that would be seen if the object were to be cut in two in a vertical plane and the nearer portion of the container removed, thereby leaving a cut face of the object exposed.

31. A device according to claim 28 further comprising means for comparing the image data in each slice with the next slice to determine any image content which is constant and appears in the same position in each slice, and enhancing the data relating thereto in the final image, or rendering the date invisible.

32. A method of detecting the mean atomic number of a mass of material within a container comprising the steps of:

(a) subjecting the material to high energy X-rays on the order of 1 MeV and determining the mean number $N_A$ of X-rays transmitted through a region thereof, (b) subjecting the same region of the material to X-rays having a significantly higher energy than the first mentioned X-rays, said higher energy being at least about 5 MeV, and determining the mean number $N_B$ of the higher energy X-rays transmitted therethrough, (c) computing the value of the ratio $N_A$ to $N_B$, and (d) determining from a look-up table and delivering as an output the average atomic number corresponding to the computed value of the $N_A/N_B$ ratio.

* * * * *